United States Patent
Kataoka et al.

(10) Patent No.: US 9,051,354 B2
(45) Date of Patent: Jun. 9, 2015

(54) PROTEIN CHARGE REGULATOR AND PROTEIN-ENCAPSULATING POLYMER MICELLE COMPLEX

(75) Inventors: Kazunori Kataoka, Tokyo (JP); Nobuhiro Nishiyama, Tokyo (JP); Yan Lee, Tokyo (JP); Takehiko Ishii, Tokyo (JP)

(73) Assignee: THE UNIVERSITY OF TOKYO, Tokyo (JP)

(*) Notice: Subject to any disclaimer, the term of this patent is extended or adjusted under 35 U.S.C. 154(b) by 53 days.

(21) Appl. No.: 13/256,605

(22) PCT Filed: Sep. 17, 2009

(86) PCT No.: PCT/JP2009/066839
§ 371 (c)(1),
(2), (4) Date: Oct. 7, 2011

(87) PCT Pub. No.: WO2010/106700
PCT Pub. Date: Sep. 23, 2010

(65) Prior Publication Data
US 2012/0046453 A1 Feb. 23, 2012

(30) Foreign Application Priority Data
Mar. 17, 2009 (JP) .................... 2009-065287

(51) Int. Cl.
*A61K 47/48* (2006.01)
*C07K 1/113* (2006.01)
*C07K 1/13* (2006.01)

(52) U.S. Cl.
CPC ............ *C07K 1/13* (2013.01); *A61K 47/48215* (2013.01); *A61K 47/48315* (2013.01)

(58) Field of Classification Search
USPC ................................. 549/233, 240
See application file for complete search history.

(56) References Cited

U.S. PATENT DOCUMENTS

| | | | |
|---|---|---|---|
| 5,256,412 A | 10/1993 | Tsunoo et al. | |
| 5,306,809 A | 4/1994 | Boon et al. | |
| 2001/0000510 A1 | 4/2001 | Sakurai et al. | |
| 2003/0220264 A1* | 11/2003 | Rozema et al. | 514/12 |
| 2007/0059271 A1 | 3/2007 | Kataoka et al. | |

FOREIGN PATENT DOCUMENTS

| | | | |
|---|---|---|---|
| JP | 2-275824 A | 11/1990 | |
| JP | 4-334377 A | 11/1992 | |
| JP | 8-188541 A | 7/1996 | |
| JP | 2004-352972 A | 12/2004 | |
| JP | 2005-529931 A | 10/2005 | |
| WO | 2005/078084 A1 | 8/2005 | |

OTHER PUBLICATIONS

Lee, Y., et al., "Charge-Conversional polyionic Complex Micelles—Efficient Nanocarriers for Protein Delivery into Cytoplasm," Angew. Chem. Int. Ed. 48:5309-5312 (Mar. 2009)—article first published online Mar. 17, 2009.*
Kanayama, N., et al., "A PEG-Based Biocompatible Block Catiomer with High Buffering Capacity for the Construction of Polyplex Micelles Showing Construction of Polyplex Micelles Showing Efficient Gene Transfer toward Primary Cells," ChemMedChem 1:439-444 (2006).*
Gruenberg, "The endocytic pathway: a mosaic of domains," Nat. Rev. 2:721-730 (2001).*
Torchilin, "Recent approaches to intracellular delivery of drugs and DNA and organelle targeting," Ann. Rev. Biomed. Eng. 343-75 (2006).*
Kanayama, N., et al., "A PEG-Based Biocompatible Block Catiomer with High Buffering Capacity for the Construction of Polyplex Micelles Showing Construction of Polyplex Micelles Showing Efficient Gene Transfer toward Primary Cells," ChemMedChem 1:439-444 (2006.*
Kam et al. "Carbon Nanotubes as Intracellular Transporters for Proteins and DNA: An Investigation of the Uptake Mechanism and Pathway" Angew. Chem. Int. Ed. 2006, vol. 45 pp. 577-581.
Lee et al. "Charge-conversional PIC micelles for the efficient protein delivery into cytoplasm" Polymer Preprints, Japan vol. 58, No. 1 (2009).
Lee et al. "Charge-Conversional Polyionic Complex Micelles-Efficient Nanocarriers for Protein Delivery into Cytoplasm", Angew. Chem. Int. Ed. 2009, vol. 48, pp. 5309-5312.
Lee et al. "Polymeric protein delivery systems" Prog. Polym. Sci. 32 (2007) pp. 669-697.
Slowing et al. "Mesoporous Silica Nanoparticles for Intracellular Delivery of Membrane-Impermable Proteins" J. Am. Chem. Soc. 2007, vol. 129, pp. 8845-8849.
Tomlinson "Next-generation protien drugs" Nature Biotechnology vol. 22, No. 5, May 2004, pp. 521-522.
Oba et al., "Nanobiotechnology and the Drug Delivery System", J. Jpn. Coll. Angiol, vol. 48 (2006) pp. 371-377, with English translation.

* cited by examiner

*Primary Examiner* — Julie Ha
*Assistant Examiner* — Kristina M Hellman
(74) *Attorney, Agent, or Firm* — Birch, Stewart, Kolasch & Birch, LLP

(57) ABSTRACT

The present invention provides a protein delivery means (e.g., a polyion complex) which allows efficient introduction into cells (particularly into the cytoplasm), is highly stable in serum, and is also widely applicable. The polyion complex of the present invention comprises a cationic polymer having a polycation moiety and a charge-conversional protein whose overall charge is converted from basic or neutral to acidic by a specific charge regulator.

18 Claims, 20 Drawing Sheets
(12 of 20 Drawing Sheet(s) Filed in Color)

(Z-average size: 113 nm, PDI = 0.264)

(A)

(B)

PROTEIN CHARGE REGULATOR AND PROTEIN-ENCAPSULATING POLYMER MICELLE COMPLEX

TECHNICAL FIELD

The present invention relates to a charge regulator for protein molecules and a polymer micelle complex encapsulating a protein, more specifically a polymer micelle complex encapsulating a protein whose overall molecular charge is regulated by such a regulator. The present invention also relates to a protein delivery device and a protein delivery kit, each comprising such a complex.

BACKGROUND ART

In the post-genomic era, the elucidation of protein functions is the most important area in the field of biology, and the development of therapeutic agents for various diseases, each comprising a protein as an active ingredient, has great potential and possibility in the field of pharmaceutical sciences. In basic studies on protein functions, various techniques have been used, including enhancement of specific protein expression or inhibition (knockdown) of protein expression. Probably, the most simple and reliable technique is to directly introduce a protein into cells. Such a direct delivery technique allows analysis of protein functions without any influence on the transcription-translation pathway. Moreover, effective in vivo protein delivery is very important, e.g., in therapeutic applications such as vaccination or protein formulations. Although various protein-based biopharmaceutical studies have been conducted, the instability of proteins in serum and the lack of a device for protein delivery into the cytoplasm have greatly limited further success (I. M. Tomlinson, Nature Biotech., 2004, vol. 22, p. 521-522). For this reason, many researchers have concentrated their efforts on the development of protein delivery techniques using hydrogels, liposomes, nanotubes, inorganic carriers or the like (K. Y. Lee et al., Prog. Polym. Sci., 2007, vol. 32, p. 669-697; N. W. S. Kam et al., Angew. Chem. Int. Ed., 2006, vol. 45, p. 577-581; I. I. Slowing et al., J. Am. Chem. Soc., 2007, vol. 129, p. 8845-8849), but any protein delivery technique has not yet been developed, which is highly efficient and highly stable in serum, and is also widely applicable.

DISCLOSURE OF THE INVENTION

Under these circumstances, there has been a demand for the development of an effective means for protein delivery into the cytoplasm.

The present invention has been made in consideration of the above situation and provides a protein charge regulator, a protein-encapsulating polymer micelle complex (polyion complex micelle), a device for intracellular protein delivery, a kit for intracellular protein delivery, etc., as shown below.

(1) A protein charge regulator, which comprises a compound represented by the following formula (I) or a derivative thereof:

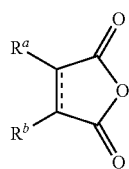

(I)

[wherein $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group. Alternatively, $R^a$ and $R^b$ may be linked to each other to form an aromatic ring or a cycloalkyl ring together with their adjacent carbon atoms. The bond between the carbon atoms adjacent to $R^a$ and $R^b$, respectively, may be either a single bond or a double bond].

Examples of a compound represented by the above formula (I) include at least one of compounds represented by the following formulae (Ia) to (Ig).

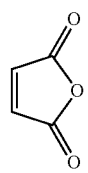

(Ia)

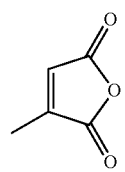

(Ib)

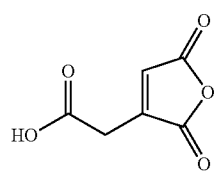

(Ic)

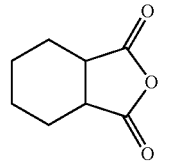

(Id)

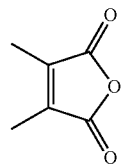

(Ie)

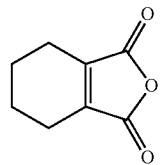

(If)

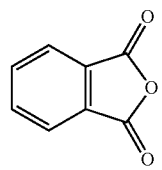

(Ig)

Examples of the charge regulator of the present invention include those which convert the overall charge of a basic or neutral protein into that of an acidic protein, more specifically those which establish binding between the compound represented by the above formula (I) or a derivative thereof and an amino group contained in a protein.

(2) A protein whose overall charge is converted by the charge regulator according to (1) above (such a protein is hereinafter referred to as a charge-conversional protein).

Examples of the charge-conversional protein of the present invention include proteins whose amino group is bound to a compound represented by the following formula (I) or a derivative thereof:

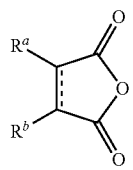
(I)

[wherein $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group. Alternatively, $R^a$ and $R^b$ may be linked to each other to form an aromatic ring or a cycloalkyl ring together with their adjacent carbon atoms. The bond between the carbon atoms adjacent to $R^a$ and $R^b$, respectively, may be either a single bond or a double bond].

Examples of a compound represented by the above formula (I) include at least one of compounds represented by the following formulae (Ia) to (Ig).

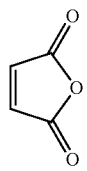
(Ia)

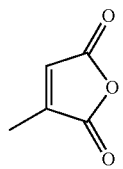
(Ib)

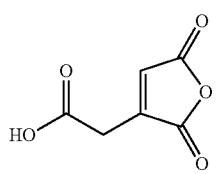
(Ic)

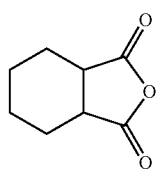
(Id)

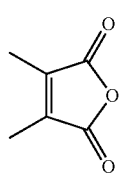
(Ie)

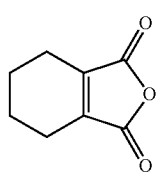
(If)

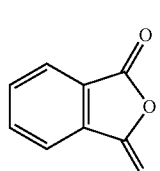
(Ig)

(3) A polyion complex, which comprises a cationic polymer at least partially having a polycation moiety and the protein according to (2) above.

Examples of the polyion complex of the present invention include those in which the above polycation moiety is a polypeptide having cationic groups in its side chains, more specifically those in which the above block copolymer is represented by the following general formula (1):

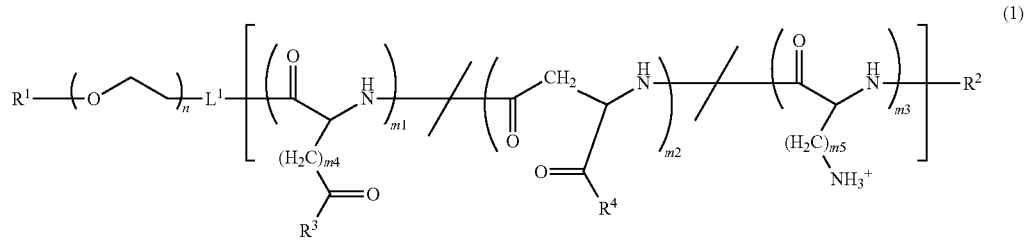
(1)

[wherein $R^1$ and $R^2$ each independently represent a hydrogen atom or an optionally substituted linear or branched alkyl group containing 1 to 12 carbon atoms, $R^3$ and $R^4$ each represent a residue derived from an amine compound having a primary amine, $L^1$ represents NH, CO, a group represented by the following general formula (4):

$$—(CH_2)_{p1}—NH—  \quad (4)$$

(wherein p1 represents an integer of 1 to 6), or a group represented by the following general formula (5):

$$-L^{2a}-(CH_2)_{q1}-L^{3a}-  \quad (5)$$

(wherein $L^{2a}$ represents OCO, OCONH, NHCO, NHCOO, NHCONH, CONH or COO, $L^{3a}$ represents NH or CO, and q1 represents an integer of 1 to 6), m1, m2 and m3 each independently represent an integer of 0 to 500 (provided that the sum of m1, m2 and m3 represents an integer of 10 to 500), m4 represents an integer of 1 to 5, m5 represents an integer of 1 to 5, and n represents an integer of 0 to 500, and the symbol "/" means that (m1+m2+m3) units of the respective monomers shown in the left and right sides of this symbol are sequenced in any order].

In the cationic polymer of the above general formula (1), examples of the group —$R^3$ and/or the group —$R^4$ include a group represented by the following general formula (2):

$$—NH—(CH_2)_r—X^1  \quad (2)$$

(wherein $X^1$ represents an amine compound residue derived from a primary, secondary or tertiary amine compound or a quaternary ammonium salt, and r represents an integer of 0 to 5), or a group represented by the following general formula (3):

$$—[NH—(CH_2)_s]_t—X^2  \quad (3)$$

(wherein $X^2$ represents an amine compound residue derived from a primary, secondary or tertiary amine compound or a quaternary ammonium salt, and s and t, which are independent of each other, represent an integer of 1 to 5 independently in each [NH—$(CH_2)_s$] unit and an integer of 2 to 5, respectively). More specific examples include —NH—$NH_2$ and —NH—$(CH_2)_2$—NH—$(CH_2)_2$—$NH_2$.

Examples of the polyion complex of the present invention include those in which the polycation moiety in the above cationic polymer is bound to the above protein through electrostatic interaction. More specific examples include those in which the above cationic polymer is a polymer further comprising a polyethylene glycol moiety, wherein the above protein and the polycation moiety in the above cationic polymer form a core region, while the polyethylene glycol moiety in the above cationic polymer forms a shell region around the core region.

Examples of the polyion complex of the present invention include those characterized in that the compound represented by the above formula (I) or a derivative thereof is eliminated from the protein released from the polyion complex upon introduction into cells, whereby the overall charge of the protein returns to its inherent charge.

(4) A device for intracellular protein delivery, which comprises the polyion complex according to (3) above.

(5) A kit for intracellular protein delivery, which comprises a cationic polymer at least partially having a polycation moiety and the charge regulator according to (1) above.

BRIEF DESCRIPTION OF THE DRAWINGS

The patent or application file contains at least one color drawing. Copies of this patent or patent application publication with color drawings will be provided by the USPTO upon request and payment of the necessary fee.

BEST MODES FOR CARRYING OUT THE INVENTION

Figure 1:
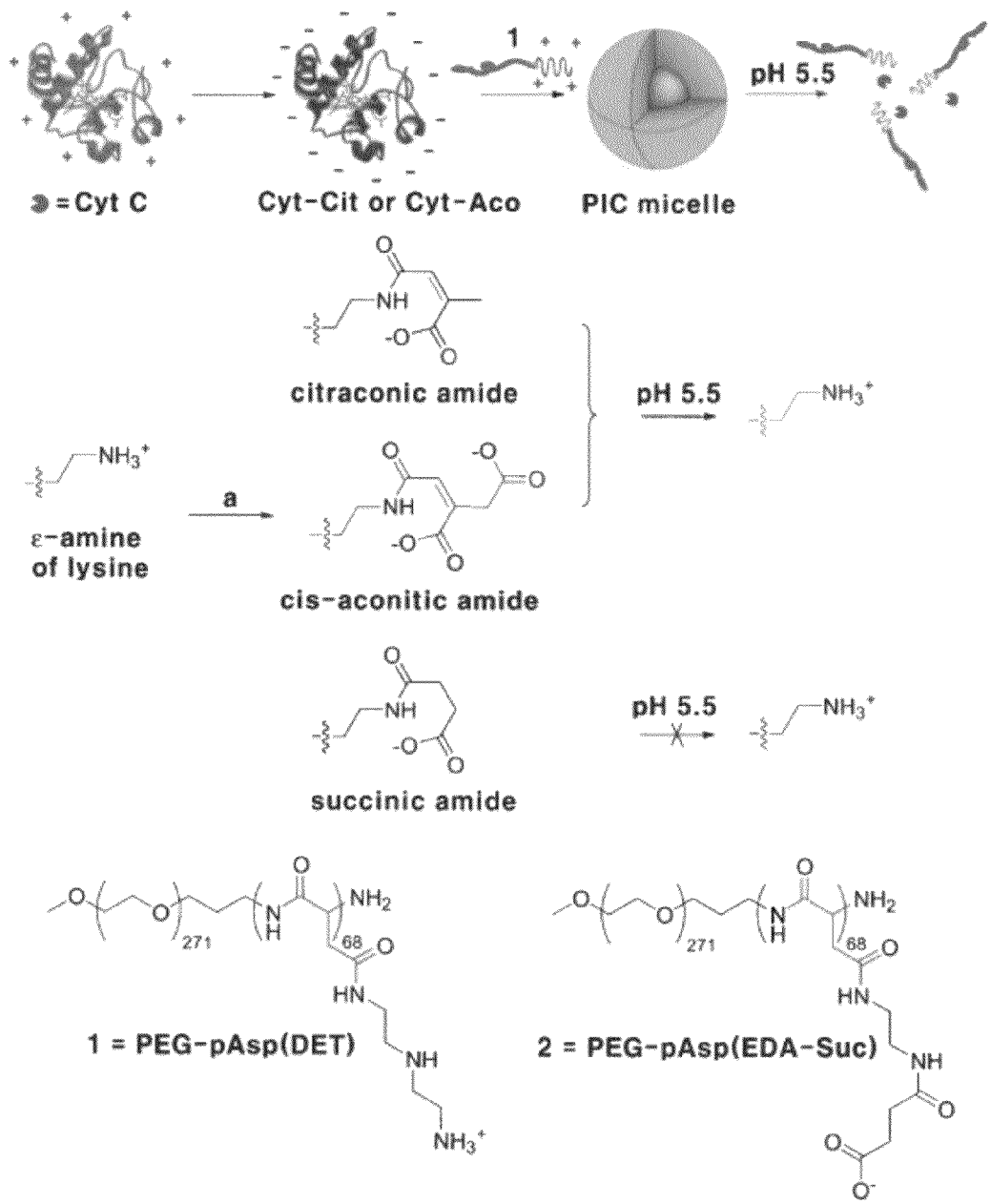
FIG. 1 schematically shows how to prepare a charge-conversional polyion complex micelle. More specifically, citraconic anhydride or cis-aconitic anhydride serving as a charge regulator is bound to an amine of a lysine residue in the cytochrome c protein to prepare cytochrome c whose overall charge is converted to negative (hereinafter referred to as a cytochrome c derivative), and this cytochrome c derivative and a given block copolymer (PEG-pAsp(DET)) serving as a cationic polymer are used to prepare polyion complex (PIC) micelles in a state encapsulating the derivative. This figure also shows that when the PIC micelles are then placed in a pH 5.5 environment, the micelles are broken down and citraconic anhydride or cis-aconitic anhydride bound as a charge regulator is eliminated from the encapsulated cytochrome c derivative, as a result of which the derivative is regenerated into the original cytochrome c.

The present invention will be described in more detail below. The scope of the present invention is not limited by the following description, and any embodiments other than those illustrated below may also be carried out with appropriate modifications without departing from the spirit of the invention.

It should be noted that this specification incorporates the specification of Japanese Patent Application No. 2009-065287 (filed on Mar. 17, 2009) in its entirety, based on which the present application claims priority. Moreover, all publications cited herein, including prior art documents, patent gazettes and other patent documents, are incorporated herein by reference.

1. Charge Regulator

As described above, the charge regulator of the present invention comprises a compound represented by the following formula (I) or a derivative thereof

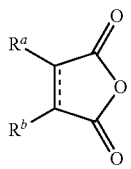
(I)

In the above formula (I), $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group. Alternatively, $R^a$ and $R^b$ may be linked to each other to form an aromatic ring or a cycloalkyl ring together with their adjacent carbon atoms. In formula (I), the bond between the carbon atoms adjacent to $R^a$ and $R^b$, respectively, may be either a single bond or a double bond, without any limitation. In formula (I), to collectively describe these two binding modes, the bond between these carbon atoms is represented by a combination of a solid line and a broken line.

More specifically, preferred compounds of the above formula (I) include compounds represented by the following formulae (Ia) to (Ig). Among them, more preferred are compounds represented by formulae (Ib) and (Ic), and even more preferred is a compound represented by formula (Ic).

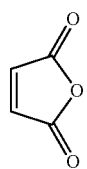
(Ia)

maleic anhydride (pH 3)

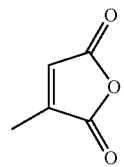
(Ib)

citraconic anhydride (pH 5.5)

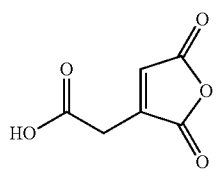
(Ic)

cis-aconitic anhydride (pH 5.5)

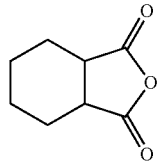
(Id)

1,2-cyclohexanedicarboxylic anhydride (pH 5.5)

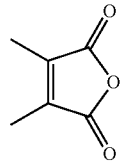
(Ie)

dimethylmaleic anhydride (pH 2)

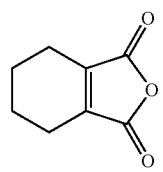
(If)

3,4,5,6-tetrahydrophthalic anhydride (pH 2)

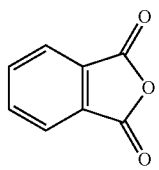
(Ig)

phthalic anhydride (pH 3)

The charge regulator of the present invention converts the overall charge of a basic or neutral protein into that of an acidic protein. In other words, the charge regulator of the present invention allows overall charge conversion by controlling the amount of charges such that a protein whose overall charge is in a positive (+) or neutral state is converted into a protein whose overall charge is negative (−). More specifically, the above overall charge conversion is preferably accomplished as follows: the compound represented by the above formula (I) or a derivative thereof is bound to an amino group (a positively charged group) contained in a protein, whereby the protein is negatively charged as a whole.

For this purpose, for example, the compound represented by the above formula (I) is bound (covalently bound) to an amino group in a protein to form a structure as represented by the following formula (I').

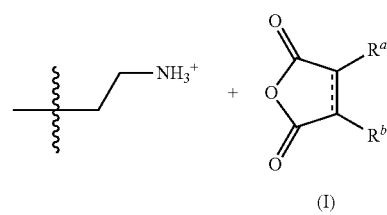
(I)

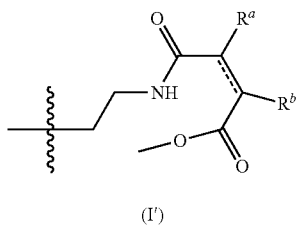

(I')

For example, if the compound represented by the above formula (I) is a compound represented by the above formula (Ib) or (Ic), the structure represented by the above formula (I') formed after binding is as shown below.

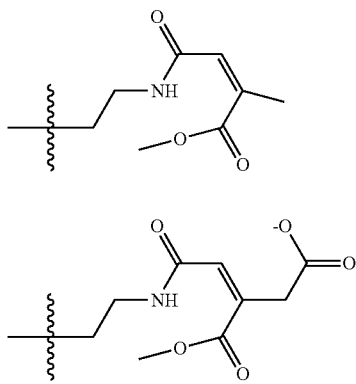

The charge regulator of the present invention can establish the above binding, for example, simply by being mixed with a protein, which is a target of overall charge conversion, in an aqueous solution, although procedures for binding reaction are not limited in any way.

Moreover, since the above binding is cleaved, for example, in a weakly acidic pH environment (e.g., within endosomes in cells), the target protein of overall charge conversion will recover its original overall charge and will regenerate its structure and activity, etc.

2. Polyion Complex

The polyion complex (PIC) of the present invention is a micellar protein-encapsulating polymer micelle complex, which comprises a specific cationic polymer (homopolymer, block copolymer, graft copolymer) and a protein treated with the charge regulator of the present invention described above (such a protein will be described in more detail later).

(1) Cationic Polymer

A specific cationic polymer, which is a member constituting the PIC of the present invention, is a cationic polymer at least partially having a polycation moiety. Such a cationic polymer may be a polymer consisting only of a polycation moiety (homopolymer), or may be a block copolymer or graft polymer having, e.g., a polyethylene glycol (PEG) moiety and a polycation moiety. The cationic polymer is not limited in any way and a preferred embodiment can be selected as appropriate, e.g., depending on the intended use of the PIC of the present invention.

The above PEG and polycation have no limitation on their structure (e.g., polymerization degree), and those of any structure can be selected. Above all, preferred as a polycation is a polypeptide having cationic groups in its side chains. It should be noted that the term "cationic group" is used here to mean not only a group which is already cationic by being coordinated with hydrogen ions, but also a group which will be cationic when coordinated with hydrogen ions. Such cationic groups include all of the known ones. A polypeptide having cationic groups in its side chains is intended to include those composed of known amino acids having a basic side chain (e.g., lysine, arginine, histidine) linked via peptide bonds, as well as those composed of various amino acids linked via peptide bonds, whose side chain (e.g., side chain of aspartic acid or glutamic acid) is substituted to have a cationic group.

More specifically, preferred examples of the above specific cationic polymer include block copolymers represented by the following general formula (1):

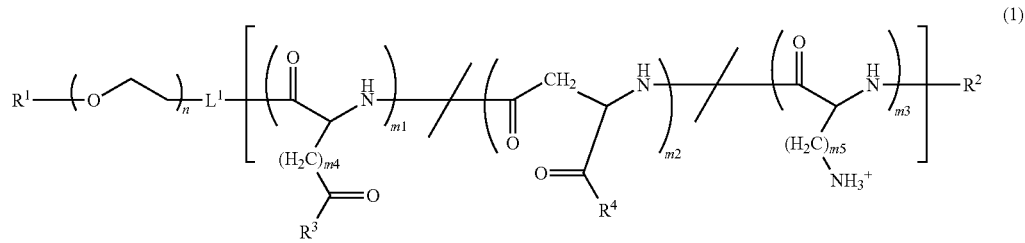

In the structural formula of general formula (1), the block moiety in which the number of repeating units (polymerization degree) is n corresponds to a PEG moiety, while the block moiety composed collectively of submoieties in which the number of repeating units is m1, m2 and m3, respectively (i.e., the moiety in brackets [ ] in general formula (1)) corresponds to a polycation moiety. Moreover, the symbol "/" appearing in the structural formula of the polycation moiety means that units of the respective monomers shown in the left and right sides of this symbol are sequenced in any order. For example, if a block moiety composed of monomer units called A and B is represented by $[-(A)_a-/-(B)_b-/-(C)_c-]$, a units of monomer A, b units of monomer B and c units of monomer C, i.e., (a+b+c) units in total of the respective monomers may be linked randomly in any order (provided that all the monomers A, B and C are linked in a straight chain).

In general formula (1), $R^1$ and $R^2$ each independently represent a hydrogen atom, or an optionally substituted linear or branched alkyl group containing 1 to 12 carbon atoms.

Examples of such a linear or branched alkyl group containing 1 to 12 carbon atoms include a methyl group, an ethyl group, a n-propyl group, an isopropyl group, a n-butyl group, a sec-butyl group, a tert-butyl group, a n-pentyl group, a n-hexyl group, a decyl group and an undecyl group, etc.

In addition, examples of possible substituents for the above alkyl group include an acetal-protected formyl group, a cyano group, a formyl group, a carboxyl group, an amino group, an alkoxycarbonyl group containing 1 to 6 carbon atoms, an acylamido group containing 2 to 7 carbon atoms, a siloxy group, a silylamino group, and a trialkylsiloxy group (in which the alkylsiloxy groups each independently contain 1 to 6 carbon atoms), etc.

If the above substituent is an acetal-protected formyl group, this substituent can be converted into a formyl group (or an aldehyde group; —CHO), which is another substituent, when hydrolyzed under acidic mild conditions. In addition, if the above substituent (particularly the substituent on $R^1$) is a formyl group or a carboxyl group or an amino group, for example, antibody or a fragment thereof or another functional or targeting protein may be bound via these groups.

In general formula (1), $R^3$ and $R^4$, each of which serves as a moiety containing a cationic group, each represent a residue derived from an amine compound having a primary amine. Examples of the groups —$R^3$ and —$R^4$ include a group represented by the following general formula (2) or (3), with a group represented by the following general formula (3) being preferred.

—NH—(CH$_2$)$_r$—X$^1$      (2)

[wherein $X^1$ represents an amine compound residue derived from a primary, secondary or tertiary amine compound or a quaternary ammonium salt, and r represents an integer of 0 to 5]

—[NH—(CH$_2$)$_s$]$_t$—X$^2$      (3)

[wherein $X^2$ represents an amine compound residue derived from a primary, secondary or tertiary amine compound or a quaternary ammonium salt, and s and t, which are independent of each other, represent an integer of 1 to 5 (preferably 2) independently in each [NH—(CH$_2$)$_s$] unit and an integer of 2 to 5 (preferably 2), respectively]

In general formulae (2) and (3), preferred examples of the terminal groups —$X^1$ and —$X^2$ (amine compound residues) include —NH$_2$, —NH—CH$_3$, —N(CH$_3$)$_2$, and groups represented by the following formulae (i) to (viii), with —NH$_2$ being particularly preferred. It should be noted that in the following formula (vi), Y may be, for example, a hydrogen atom, an alkyl group (containing 1 to 6 carbon atoms), or an aminoalkyl group (containing 1 to 6 carbon atoms), etc.

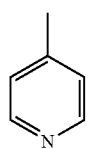
(i)

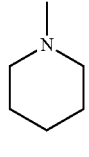
(ii)

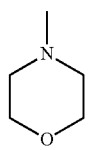
(iii)

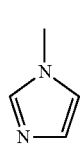
(iv)

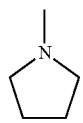
(v)

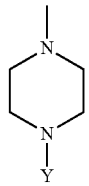
(vi)

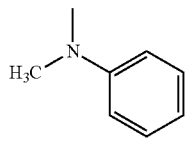
(vii)

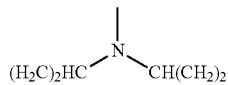
(viii)

In general formula (1), particularly preferred as the group —$R^3$ or —$R^4$ is "—NH—NH$_2$" or "—NH—(CH$_2$)$_2$—NH—(CH$_2$)$_2$—NH$_2$" and more preferred is the latter containing an ethylenediamine unit. It should be noted that "—NH—(CH$_2$)$_2$—NH—(CH$_2$)$_2$—NH$_2$" listed above is capable of electrostatically interacting with a protein to be encapsulated because it has two pKa values of 6.0 and 9.5, and is in a gauche-type single protonated state at pH 7.4 where complex formation occurs (see Reaction Scheme 1 shown below). On the other hand, in endosomes (at pH 5.5), "—NH—(CH$_2$)$_2$—NH—(CH$_2$)$_2$—NH$_2$" will be further protonated and converted into an anti state (see Reaction Scheme 1 shown below). Thus, "—NH—(CH$_2$)$_2$—NH—(CH$_2$)$_2$—NH$_2$" has the effect of facilitating endosomal escape, based on its buffering effect.

Reaction Scheme 1

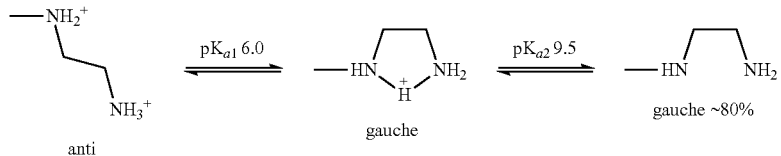

In general formula (1), $L^1$ serving as a linker represents NH, CO, a group represented by the following general formula (4):

$$—(CH_2)_{p1}—NH— \quad (4)$$

[wherein p1 represents an integer of 1 to 6 (preferably 2 to 3)], or a group represented by the following general formula (5):

$$-L^{2a}-(CH_2)_{q1}-L^{3a}- \quad (5)$$

[wherein $L^{2a}$ represents OCO, OCONH, NHCO, NHCOO, NHCONH, CONH or COO, $L^{3a}$ represents NH or CO, and q1 represents an integer of 1 to 6 (preferably 2 to 3)].

In general formula (1), n represents the number of repeating units (polymerization degree) in the PEG moiety, and more specifically represents an integer of 0 to 500 (preferably 100 to 400, more preferably 200 to 300).

Moreover, m1, m2 and m3, each of which represents the polymerization degree of each monomer unit constituting the polycation moiety, each independently represent an integer of 0 to 500 (preferably 0 to 100, more preferably 10 to 100, even more preferably 20 to 100, still even more preferably 30 to 100) (provided that the sum of m1, m2 and m3 (i.e., m1+m2+m3) is 10 to 500 (preferably 10 to 300, more preferably 20 to 200, even more preferably 30 to 150, still even more preferably 40 to 120, yet still even more preferably 50 to 100, particularly preferably 60 to 70)).

Further, with respect to the number of repeating methylene (—$CH_2$—) units in each side chain of the polycation moiety, m4 represents an integer of 1 to 10 (preferably 1 to 5, more preferably 3 to 4, even more preferably 1 to 2), while m5 represents an integer of 1 to 10 (preferably 1 to 5, more preferably 3 to 4, even more preferably 1 to 2).

In view of the foregoing, the cationic polymer represented by general formula (1) can be regarded as a polymer composed of the following two block moieties:

a block moiety having side chains each electrostatically binding to a protein to be encapsulated (i.e., block moiety whose polymerization degree is "m1+m2+m3" and which has cationic groups in its side chains: polycation moiety); and a block moiety consisting of a polyethylene glycol (PEG) chain which is hydrophilic and highly biocompatible (i.e., block moiety whose polymerization degree is n: PEG moiety).

The molecular weight (Mw) of the cationic polymer represented by general formula (1) is not limited in any way, but it is preferably 23,000 to 45,000, more preferably 28,000 to 34,000. Moreover, with respect to the respective block moieties, the PEG moiety preferably has a molecular weight (Mw) of 8,000 to 15,000, more preferably 10,000 to 12,000, while the polycation moiety preferably has a molecular weight (Mw) of 15,000 to 30,000, more preferably 18,000 to 22,000, as a whole.

The cationic polymer represented by general formula (1) may be prepared in any manner. For example, a segment comprising $R^1$ and the block moiety of PEG chain (PEG segment) is synthesized in advance, to one end (opposite to $R^1$) of which is then sequentially polymerized with given monomers, optionally followed by substituting or converting each side chain to contain a cationic group, or alternatively, the above PEG segment and a block moiety containing cationic groups in its side chains are synthesized in advance, which are then linked to each other. Procedures and conditions for each reaction in these preparation methods may be selected or determined as appropriate in consideration of standard processes.

The above PEG segment may be prepared, for example, by using procedures for preparing a PEG segment moiety in the block copolymer described in WO 96/32434, WO 96/33233 and WO 97/06202, etc. In the PEG segment, the end opposite to the group —$R^1$ corresponds to a moiety serving as "-$L^1$" in general formula (1), and is preferably —$NH_2$, —COOH, a group represented by the following general formula (6):

$$—(CH_2)_{p2}—NH_2 \quad (6)$$

[wherein p2 represents an integer of 1 to 5 (preferably 2 to 3)], or a group represented by general formula (7):

$$-L^{2b}-(CH_2)_{q2}-L^{3b} \quad (7)$$

[wherein $L^{2b}$ represents OCO, OCONH, NHCO, NHCOO, NHCONH, CONH or COO, $L^{3b}$ represents $NH_2$ or COOH, and q2 represents an integer of 1 to 6 (preferably 2 to 3)].

Detailed procedures for preparation of the cationic polymer represented by general formula (1) are as follows, by way of example: a PEG segment derivative having an amino group at its end is used, and this amino end is polymerized with N-carboxylic acid anhydrides (NCAs) of protected amino acids (e.g., (β-benzyl-L-aspartate (BLA) and Nε-Z-L-lysine) to synthesize a block copolymer, followed by substituting or converting the side chain of each block moiety with diethylenetriamine (DET) or the like such that the side chain has a cationic group, as described above.

(2) Charge-Conversional Protein

In the PIC of the present invention, the protein serving as a component of the core region may be any protein whose overall charge is converted by the charge regulator of the present invention described above (charge-conversional protein), more specifically any protein whose overall charge is converted from positive or neutral (as found in a basic or neutral protein) to negative (as found in an acidic protein). Such a protein whose overall charge is converted to negative can be regarded as an anionic substance (polyanion) when the protein is taken as a whole. Thus, such a protein can easily form a micellar complex, which is inherently difficult to form in a basic or neutral protein, through electrostatic interaction with the polycation moiety in the above cationic polymer.

The protein used in the present invention may be of any type as long as it is originally included in basic or neutral proteins. The protein used in the present invention encompasses not only simple proteins, but also glycoproteins and lipoproteins, etc. Moreover, the protein used in the present invention is not limited to those consisting of full-length amino acid sequences, and encompasses their partial fragments and peptides, as well as proteins consisting of two molecules (dimers) or more molecules, and fusion proteins between partial or full-length sequences thereof. The protein used in the present invention is also not limited to those composed of natural amino acids, and encompasses modified proteins containing at least some unnatural amino acids as constituent members. Further, the protein used in the present invention encompasses, as appropriate, those modified to have various labeling substances or the like, if necessary.

Specific examples of the protein used in the present invention include various enzymes, antibodies (e.g., antibodies against nuclear pore complexes) or antibody fragments, etc. In the context of the present invention, antibody fragments include, but are not limited to, Fab, Fab', F(ab')$_2$ (also expressed as (Fab')$_2$), Fv (variable fragment of antibody), single chain antibody (e.g., H chain, L chain, H chain V region, and L chain V region), scFv, diabody (scFv dimer), dsFv (disulfide stabilized V region), as well as peptides at least partially containing complementarity determining regions (CDRs). The preparation of these antibody fragments is summarized below.

Fab is an antibody fragment having a molecular weight of about 50,000 and having antigen-binding activity, which is composed of the N-terminal half of H chain and the full length of L chain linked via a disulfide bond, among fragments obtained by treating an antibody molecule with a protease, papain. Alternatively, Fab may also be prepared as follows: DNA encoding antibody Fab is inserted into a prokaryotic or eukaryotic expression vector, and this vector is introduced into a prokaryotic or eukaryotic organism for expression.

F(ab')$_2$ is an antibody fragment having a molecular weight of about 100,000 and having antigen-binding activity, which is slightly larger than that composed of Fab fragments linked via disulfide bonds in the hinge region, among fragments obtained by treating an antibody molecule with a protease, pepsin. Alternatively, F(ab')$_2$ may also be prepared by linking Fab' fragments described later via a thioether bond or a disulfide bond.

Fab' is an antibody fragment having a molecular weight of about 50,000 and having antigen-binding activity, which is obtained by cleaving the disulfide bonds in the hinge region of the above F(ab')$_2$. Alternatively, Fab' may also be prepared as follows: DNA encoding an antibody Fab' fragment is inserted into a prokaryotic or eukaryotic expression vector, and this vector is introduced into a prokaryotic or eukaryotic organism for expression.

scFv is an antibody fragment having antigen-binding activity, which is composed of a single H chain V region (VH) and a single L chain V region (VL) linked via an appropriate peptide linker (P), i.e., a VH-P-VL or VL-P-VH polypeptide. For preparation of scFv, cDNAs encoding antibody VH and VL may be obtained to construct DNA encoding scFv, and this DNA may be inserted into a prokaryotic or eukaryotic expression vector, followed by introducing this expression vector into a prokaryotic or eukaryotic organism for expression.

Diabody is an antibody fragment composed of dimerized scFv fragments and having divalent antigen-binding activity. The divalent antigen-binding activity may be directed to the same or different antigens. For preparation of diabody, cDNAs encoding antibody VH and VL may be obtained to construct DNA encoding scFv such that the amino acid sequence of P has a length of 8 residues or less, and this DNA may be inserted into a prokaryotic or eukaryotic expression vector, followed by introducing this expression vector into a prokaryotic or eukaryotic organism for expression.

dsFv is an antibody fragment composed of VH and VL polypeptides, in each of which a single amino acid residue is replaced with a cysteine residue and which are linked via a disulfide bond between these cysteine residues. An amino acid residue to be replaced with a cysteine residue can be selected based on three-dimensional structure prediction of antibody according to the method reported by Reiter et al. (Protein Engineering, vol. 7, p. 697-704, 1994). For preparation of dsFv, cDNAs encoding antibody VH and VL may be obtained to construct DNA encoding dsFv, and this DNA may be inserted into a prokaryotic or eukaryotic expression vector, followed by introducing this expression vector into a prokaryotic or eukaryotic organism for expression.

A CDR-containing peptide is configured to comprise at least one or more CDR regions in VH or VL. In the case of a peptide containing a plurality of CDRs, these CDRs may be linked directly or through an appropriate peptide linker. For preparation of a CDR-containing peptide, DNA encoding CDR in antibody VH or VL may be constructed, and the DNA may be inserted into a prokaryotic or eukaryotic expression vector, followed by introducing this expression vector into a prokaryotic or eukaryotic organism for expression. Alternatively, a CDR-containing peptide may also be prepared by chemical synthesis such as Fmoc (fluorenylmethyloxycarbonyl) and tBoc (t-butyloxycarbonyl) methods.

In the charge-conversional protein used in the present invention, the above compound represented by formula (I) or a derivative thereof is bound to an amino group contained in the protein. With respect to this binding, the same description as given in Section 1 above can also apply.

As described above, the charge-conversional protein molecule serves as a polyanion and hence is capable of binding to side chains of the polycation moiety in the cationic polymer through electrostatic interaction.

In the present invention, various substances exerting their functions in cells may be incorporated into the core region together with the above charge-conversional protein, if necessary. For example, high-molecular-weight or low-molecular-weight "anionic substances" may be used, more specifically including polymeric substances such as peptide hormones, proteins, enzymes and nucleic acids (DNA, RNA or PNA), as well as small substances (water-soluble compounds) having charged functional groups in their molecules, etc. It should be noted that such anionic substances also include molecules with a plurality of differently charged functional groups (anionic and cationic groups), whose overall charged state can be changed to anionic by varying pH. These anionic substances may be used either alone or in combination, without any limitation.

(3) Polyion Complex (PIC)

The PIC of the present invention can be regarded as a core-shell type micellar complex in such a state where the charge-conversional protein and a part (polycation moiety) of the above cationic polymer form a core region through their electrostatic interaction, and other parts (including the PEG moiety) in the cationic polymer form a shell region around the core region.

The PIC of the present invention can be easily prepared, for example, by mixing the charge-conversional protein and the cationic polymer in any buffer (e.g., Tris buffer).

The mixing ratio between the cationic polymer and the charge-conversional protein is not limited in any way, but in the present invention, for example, the ratio between the total number (N) of cationic groups (e.g., amino groups) in the block copolymer and the total number (C) of carboxyl groups in the charge-conversional protein (N/C ratio) may be set to 0.1 to 200, particularly 0.5 to 100, and more particularly 1 to 50. If the N/C ratio is in the above range, it is preferred in that free molecules of the cationic polymer can be reduced. It should be noted that the above cationic groups (N) are intended to mean groups capable of electrostatic interaction and ionic bonding with carboxyl groups in the charge-conversional protein to be encapsulated within the micelle.

Although the PIC of the present invention is of any size, for example, the particle size is preferably 5 to 200 nm, more preferably 10 to 100 nm, as measured by dynamic light scattering (DLS).

Upon introduction into cells, the PIC of the present invention releases the above charge-conversional protein encapsulated therein. In this case, the compound represented by the above formula (I) or a derivative thereof is dissociated (cleaved) from the protein in response to changes in the pH environment within the cytoplasm (which is changed to a weakly acidic environment (e.g., around pH 5.5)). As a result, the overall charge of the protein returns to the original charge (overall charge) inherent to the protein, so that the protein can be present within the recipient cells in a state where its structure and activity, etc. are regenerated.

3. Protein Delivery Device

The present invention provides a protein delivery device which comprises the above polyion complex (PIC). The protein delivery device of the present invention can be used as a means for efficiently introducing a desired protein (charge-conversional protein) encapsulated within the core region of PIC into target cells, with the aid of changes in the oxidation-reduction environment between inside and outside of the cells.

More specifically, a solution containing PIC encapsulating a desired protein is administered to an animal subject and taken up into target cells in the body. Then, once the PIC taken up into the cells reaches endosomes, the charge regulator will be eliminated from the protein to cause a change in the charge balance within the PIC, whereby the PIC will be broken down. Once the PIC is broken down, the protein will be released from the PIC, and at the same time, the polymer dissociated from the PIC will damage the endosomal membrane. As a result, the endosomes are destructed to achieve delivery of the released protein into the cytoplasm (see FIG. 6).

The protein delivery device of the present invention may be applied to various mammals including, but not limited to, humans, mice, rats, rabbits, pigs, dogs and cats. For administration to an animal subject, parenteral modes such as intravenous drip infusion are usually selected, and conditions (e.g., dosage, administration frequency and administration period) may be determined as appropriate for the type and condition of animal subject.

The protein delivery device of the present invention can be used in therapies (e.g., enzyme replacement therapy, antibody-based immunotherapy) in which a desired protein is introduced into cells responsible for various diseases. Thus, the present invention can also provide a pharmaceutical composition (e.g., for enzyme replacement therapy or immunotherapy) containing the above PIC, as well as a method (e.g., enzyme replacement therapy or antibody-based immunotherapy) for treatment of various diseases using the above PIC. It should be noted that the administration mode and conditions are the same as those described above.

The above pharmaceutical composition can be prepared in a standard manner by using appropriately selected excipients, fillers, extenders, binders, wetting agents, disintegrants, lubricants, surfactants, dispersants, buffering agents, preservatives, solubilizers, antiseptics, correctives, soothing agents, stabilizers and isotonizing agents, etc., which are commonly used for drug preparation. Moreover, the pharmaceutical composition may usually be in the dosage form of intravenous injections (including drip infusions) and is provided in the form of unit dose ampules or multi-dose containers, by way of example.

4. Protein Delivery Kit

The protein delivery kit of the present invention comprises the above specific cationic polymer and the charge regulator of the present invention described above. This kit can be preferably used, for example, in various therapies using a desired protein (e.g., enzyme replacement therapy, antibody-based immunotherapy).

In the kit of the present invention, the cationic polymer may be stored in any state, and a solution or powder state may be selected in consideration of its stability (storage quality) and easiness of use, etc.

The kit of the present invention may further comprise other components, in addition to the above specific cationic polymer and charge regulator. Examples of other components include various buffers, various proteins to be introduced into cells (charge-conversional proteins), dissolution buffers, and instructions for use (instruction manual), etc.

The kit of the present invention is used to prepare a polyion complex (PIC) whose core region is formed from a desired protein to be introduced into target cells, and the PIC thus prepared can be effectively used as a device for protein delivery into target cells.

The present invention will be further described in more detail by way of the following illustrative examples, which are not intended to limit the scope of the invention.

Example 1

1. Materials

N,N-Dimethylformamide (DMF) (WAKO, Wako Pure Chemical Industries, Ltd., Japan)

Dichloromethane (DCM) (WAKO. Japan)

Ethylenediamine (1,2-diaminoethane) (Tokyo Chemical Industry Co. Ltd., Japan)

Diethylenetriamine (bis(2-aminoethyl)amine), which was purchased from Tokyo Chemical Industry Co. Ltd. (Japan) and distilled again before use.

Acetic acid, citraconic anhydride, succinic anhydride and hydrochloric acid, which were purchased from WAKO, (Japan) and used without further purification.

1-Methyl-2-pyrrolidinone (NMP) and cis-aconitic anhydride, which were purchased from ALDRICH (USA).

α-Methoxy-ω-aminopoly(ethylene glycol) (molecular weight=12,000) and β-benzyl-L-aspartate-N-carboxy-anhydride (BLA-NCA), which were available from NOF Corporation (Japan).

Horse heart cytochrome c, which was available from Calbiochem (USA).

2. Synthesis of Cationic Polymer

As a cationic polymer having a PEG moiety and a polycation moiety, PEG-pAsp(DET) (PEG-{N—[N'-(2-aminoethyl)-2-amino ethyl]aspartamide}) was synthesized in the following manner (see Scheme 1 shown below).

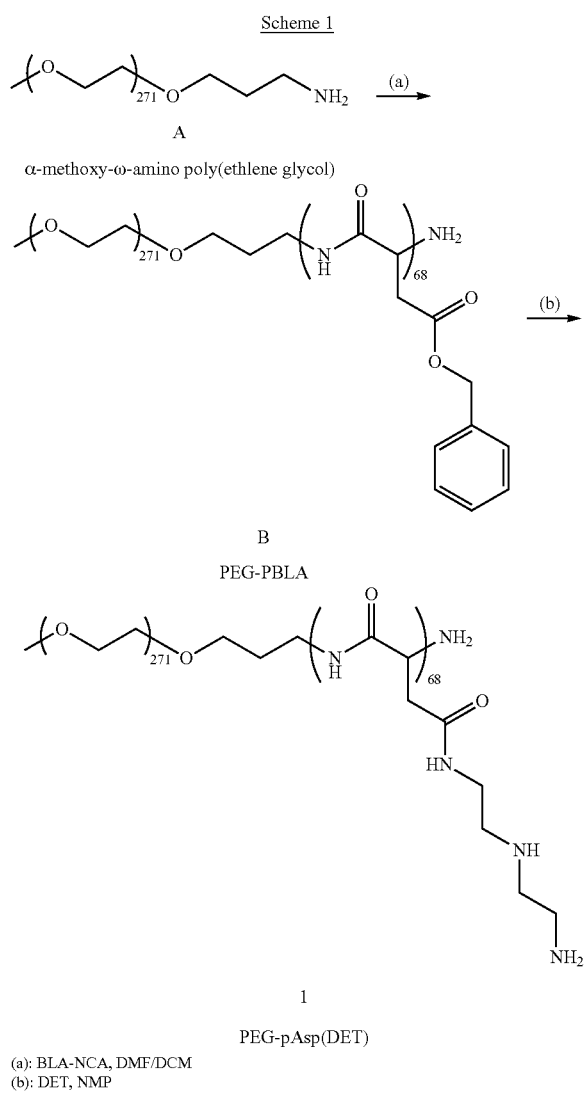

Scheme 1

A
α-methoxy-ω-amino poly(ethlene glycol)

B
PEG-PBLA

1
PEG-pAsp(DET)

(a): BLA-NCA, DMF/DCM
(b): DET, NMP (1) Synthesis of PEG-PBLA (PEG-poly(β-benzyl-L-aspartate)) (B in Scheme 1)

PEG-PBLA can be obtained by ring-opening polymerization of BLA-NCA, starting from the terminal amino group of α-methoxy-ω-aminopoly(ethylene glycol) (A in Scheme 1). This PEG macro-initiator (500 mg; 0.0417 mmol) was dissolved in 5 mL of DMF/DCM (1:10). 8 mL of a BLA-NCA solution (780 mg; 3.13 mmol) in DMF/DCM (1:10) was added to the PEG macro-initiator solution, and the reaction mixture was stirred under an argon atmosphere at 35° C. for 48 hours. The resulting polymer was precipitated in diethyl ether (150 mL). This precipitate was washed twice with diethyl ether to give 1.1 g of a white powder. To determine the molecular weight of PEG-PBLA, PEG-PBLA was converted into PEG-pAsp with 0.5 M NaOH (Harada, A. and Kataoka, K., *J. Am. Chem. Soc.*, 2003, vol. 125, p. 15306-15307). The GPC chromatogram of the converted PEG-pAsp showed a single mode, and $M_w/M_n$, was determined to be 1.01 from a calibration curve of PEG standards. Based on $^1$H NMR data (see below), the polymerization degree (DP) of BLA units was calculated to be 68. All NMR spectra were recorded at 300 MHz with a JEOL EX 300 spectrometer. Chemical shifts were reported in ppm down field from tetramethylsilane.

$^1$H NMR (CDCl$_3$): δ2.63-3.05 (136H, COCHCH$_2$COOCH$_2$Ph), δ3.32 (3H, CH$_3$OCH$_2$CH$_2$), δ3.55 (1092H, OCH$_2$CH$_2$O), δ4.23 (68H, COCHNH), δ5.06 (136H, COOCH$_2$Ph), δ7.20 (340H, COOCH$_2$Ph), δ8.79 (68H, COCHNH).

(2) Synthesis of PEG-pAsp(DET) (1 in Scheme 1)

PEG-PBLA (300 mg; 0.802 mmol of benzyl ester) obtained in (1) above was dissolved in NMP (10 mL). To this solution, diethylenetriamine (40.1 mmol) was added and the reaction mixture was stirred at 10° C. for 2 hours. The resulting solution was added dropwise to a 10% aqueous acetic acid solution (30 mL). The neutralized solution was dialyzed at 4° C. against 0.01 M hydrochloric acid (three times) and distilled water (three times). As a lyophilized hydrochloride salt, a white powder of PEG-pAsp(DET) was obtained. In $^1$H NMR (see below), there was no peak for benzyl groups.

$^1$H NMR (D$_2$O): δ2.63 (272H, COCHCH$_2$CONHCH$_2$CH$_2$NHCH$_2$CH$_2$NH$_2$, COCH$_2$CHCONHCH$_2$CH$_2$NHCH$_2$CH$_2$NH$_2$ and COCHCH$_2$CONHCH$_2$CH$_2$NHCH$_2$CH$_2$NH$_2$), δ2.76 (136H, COCHCH$_2$CONHCH$_2$CH$_2$NHCH$_2$CH$_2$NH$_2$), δ2.94 (136H, COCHCH$_2$CONHCH$_2$CH$_2$NHCH$_2$CH$_2$NH$_2$), δ3.20-3.50 (139H, CH$_3$OCH$_2$CH$_2$ and COCHCH$_2$CONHCH$_2$CH$_2$NHCH$_2$CH$_2$NH$_2$), δ3.53 (1092H, OCH$_2$CH$_2$O), δ4.57 (68H, COCHCH$_2$CONHCH$_2$CH$_2$NHCH$_2$CH$_2$NH$_2$ and COCH$_2$CHCONHCH$_2$CH$_2$NHCH$_2$CH$_2$NH$_2$)

3. Modification (Overall Charge Conversion) of Cytochrome C

Horse heart cytochrome c (10 mg) was dissolved in 0.5 M NaHCO$_3$ buffer (pH 9.0, 5 mL) and stirred at 4° C. for 30 minutes, followed by slow addition of citraconic anhydride (104 mg). After stirring for 2 hours, the mixture was purified with an Amicon Ultra (MWCO=10,000; MILLIPORE (Billerica, Mass.)) (using three volumes of distilled water). As a product, a cytochrome c derivative (Cyt-Cit), which was modified to have citraconic amide by binding citraconic anhydride to the above cytochrome c, was obtained as a lyophilized red powder (see FIG. 1). Except that citraconic anhydride was replaced with cis-aconitic anhydride and succinic anhydride, the same procedure was repeated to give a cytochrome c derivative (Cyt-Aco) which was modified to have cis-aconitic amide by binding cis-aconitic anhydride to the above cytochrome c, as well as a cytochrome c derivative (Cyt-Suc) which was modified to have succinic amide by binding succinic anhydride to the above cytochrome c (see FIG. 1).

Wild-type horse heart cytochrome c (CytC) and the resulting cytochrome c derivatives (Cyt-Cit and Cyt-Aco) were measured for their charge density and other properties. The results obtained are shown in Table 1 below.

TABLE 1

|  | Charge density (Da/charge) | Particle size (nm) | PDI |
| --- | --- | --- | --- |
| CytC | +825 | N.D. | N.D. |
| Cyt-Cit | −484 | 43.3 | 0.046 |
| Cyt-Aco | −296 | 50.1 | 0.055 |

It should be noted that the charge density data in Table 1 was calculated from the amino acid sequence of each cytochrome c, and the particle size and polydispersity index (PDI) were measured at 25° C. with a Zetasizer Nano ZS (Malvern Instruments Ltd., Malvern, UK).

4. Preparation of PICs

The cationic polymer (PEG-pAsp(DET)) obtained in 2 above and the cytochrome c derivative (Cyt-Cit or Cyt-Aco) obtained in 3 above were used to prepare PIC micelles in the following manner.

The cytochrome c derivative (0.50 mg/mL) and the above cationic polymer (1.0 mg/mL) were each dissolved in distilled water. The resulting respective solutions were each filtered through a 0.1 μm syringe filter and mixed together at a specific N/C ratio (more specifically N/C=2) to thereby obtain PIC micelles encapsulating the above cytochrome c derivative (Cyt-Cit or Cyt-Aco). It should be noted that in the following experiments, the above mixed solution was supplemented as appropriate with acetate buffer (pH 5.5) or phosphate buffer (pH 7.4). The final NaCl concentration in the mixed solution was set to 150 mM.

Figure 2:
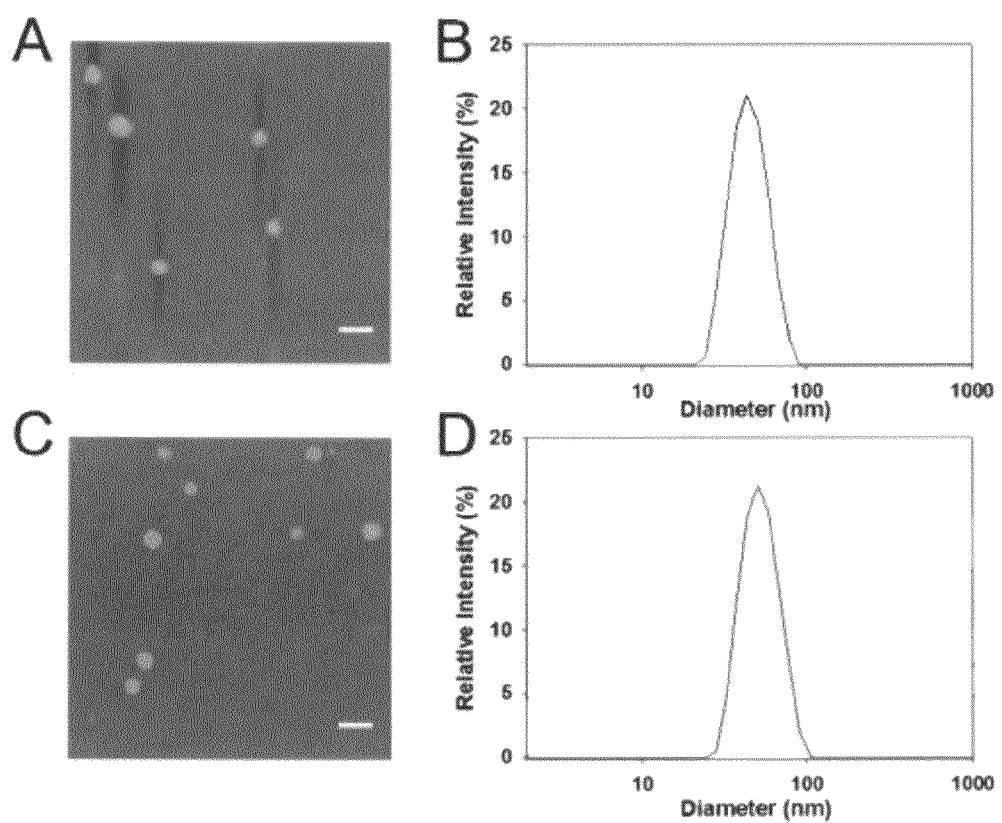
FIG. 2 shows PIC micelles (N/C ratio=2) formed from a cytochrome c derivative and a given block copolymer (PEG-pAsp(DET)) serving as a cationic polymer. More specifically, panels A and C show images of PIC micelles, as observed under an atomic force microscope (AMF) (where the white scale bars each represent 200 nm), while panels B and D show the particle size distribution of PIC micelles, as measured by dynamic light scattering (DLS). The PIC micelles in A and B were obtained with the use of citraconic anhydride as a charge regulator, while the PIC micelles in C and D were obtained with the use of cis-aconitic anhydride as a charge regulator.

The resulting PIC micelles were analyzed with an atomic force microscope (AMF) (Nanoscope Ma multimode, Nippon Veeco Co. Tokyo Japan) for imaging of their morphology. In addition, the resulting PIC micelles were measured for their particle size by dynamic light scattering (DLS) (Zetasizer Nano-ZS (green badge, ZEN3500, MALVERN INSTRUMENTS, Malvern, Ltd. Malvern, U. K.); equipped with a 532 nm green laser). The results obtained are shown in FIG. 2.

5. Observation of PIC Micelles Under an Atomic Force Microscope (AMF) (FIG. 2)

A solution of the PIC micelles obtained in 4 above (PBS, pH 7.4, 150 mM NaCl) was placed in a volume of 2 μl on a silicon wafer disk. After adsorption at room temperature for 10 minutes, the excess solution was removed with a filter paper and the disk surface was dried at room temperature. The PIC micelles were observed under an AMF in tapping mode at an excitation frequency range of 7.8 to 7.9 kHz. The results obtained are shown in FIG. 2.

6. Particle Size Measurement of PIC Micelles by Dynamic Light Scattering (DLS) (FIG. 2)

A solution of the PIC micelles obtained in 4 above was adjusted to contain the cytochrome c derivative (Cyt-Cit or Cyt-Aco) at a content of 0.125 mg/mL, and then incubated at 37° C. The particle size (particle size distribution) of the PIC micelles was measured by dynamic light scattering (DLS) with a Zetasizer Nano-ZS (green badge, ZEN3500, MALVERN INSTRUMENTS, Malvern, Ltd. Malvern, U. K.) equipped with a 532 nm green laser. The results obtained are shown in FIG. 2.

7. Decomposition of Citraconic Amide and Cis-Aconitic Amide in Cytochrome c derivatives (Cyt-Cit and Cyt-Aco) (FIG. 3)

The decomposition rate of citraconic amide was measured by the fluorescamine method. Fluorescamine is a fluorescent dye reactive to an amine (maximum fluorescence wavelength: 465 mm). Since major amines in lysine groups will be exposed after decomposition of citraconic amide and cis-aconitic amide in the cytochrome c derivatives, their decomposition rate can be calculated when comparing fluorescence between before and after incubation. For analysis, a Nanodrop® ND-3300 fluorospectrometer (NanoDrop Technologies; Wilmington, Del.) was used.

A sample of each cytochrome c derivative was dissolved in distilled water at a concentration of about 1 mg/mL. 100 μL of this stock solution was mixed with 100 μL of acetate buffer (10 mM) at pH 5.5. This solution was incubated at 37° C. and a 10 μL aliquot was diluted every 1 hour with 100 μL of dimethyl sulfoxide (DMSO) (2% triethylamine (TEA)). This mixture was added to 10 μL of a fluorescamine solution in DMF (5 mg/mL) and incubated at room temperature for 10 minutes. The fluorescence was measured at a fluorescence wavelength of 465 nm. The excitation light source used was UV light (365 nm to 400 nm) in the fluorospectrometer. Fluorescence observed for a sample in which cytochrome c derivative was incubated overnight in 0.01 M HCl was used to determine all exposed amines (100%). Moreover, fluorescence observed for a blank buffer solution serving as a negative control was used to determine no exposed amine (0%).

Figure 3:
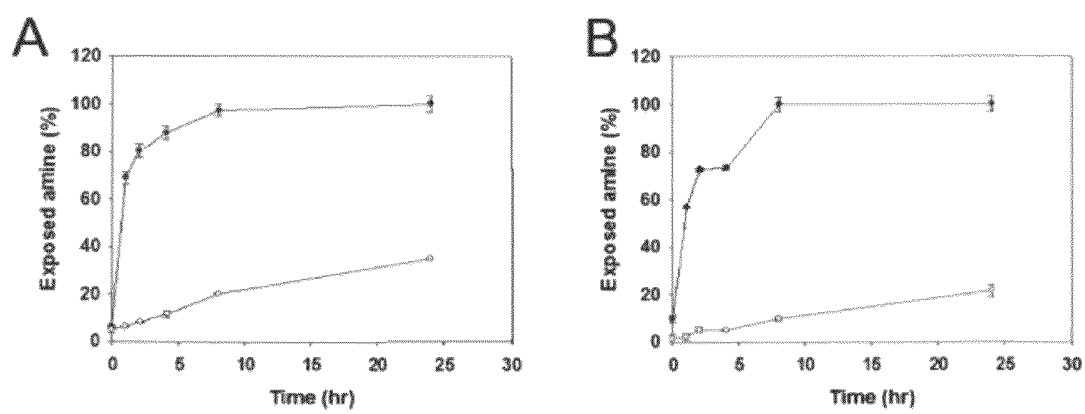
FIG. 3 shows the decomposition rate of cytochrome c derivatives. More specifically, panel A shows a cytochrome c derivative (Cyt-Cit) obtained with the use of citraconic anhydride as a charge regulator, while panel B shows a cytochrome c derivative (Cyt-Aco) obtained with the use of cis-aconitic anhydride as a charge regulator. In the figure, open plots (◯; open circles) represent the decomposition rate in a pH 7.4 environment (under physiological conditions), while closed plots (●; closed circles) represent the decomposition rate in a pH 5.5 environment.

The results obtained are shown in FIG. 3.

8. Fluorescent Labeling of Cytochrome c Derivatives

Fluorescently labeled cytochrome c derivatives (Cyt-Cit, Cyt-Aco and Cyt-Suc) were prepared for measurement of breakdown of PIC micelles and for observation of intracellular delivery. Horse heart cytochrome c was dissolved in 0.1 M NaHCO₃ buffer (pH 8.5) and stirred at 4° C. for 30 minutes. To this solution, Alexa-Fluor 488 carboxylic acid, succinimidyl ester (Invitrogen, USA) (five volumes of cytochrome c; 10 mg/mL in DMSO) was added and stirred at 4° C. for 2 hours. This reaction mixture was purified with an Amicon Ultra (MWCO=10,000; MILLIPORE (Billerica, Mass.)) (three times with distilled water). The fluorescently labeled cytochrome c derivatives were obtained after lyophilization. It should be noted that the cytochrome c derivatives (Cyt-Cit, Cyt-Aco and Cyt-Suc) used were those obtained in 3 above.

Figure 4:
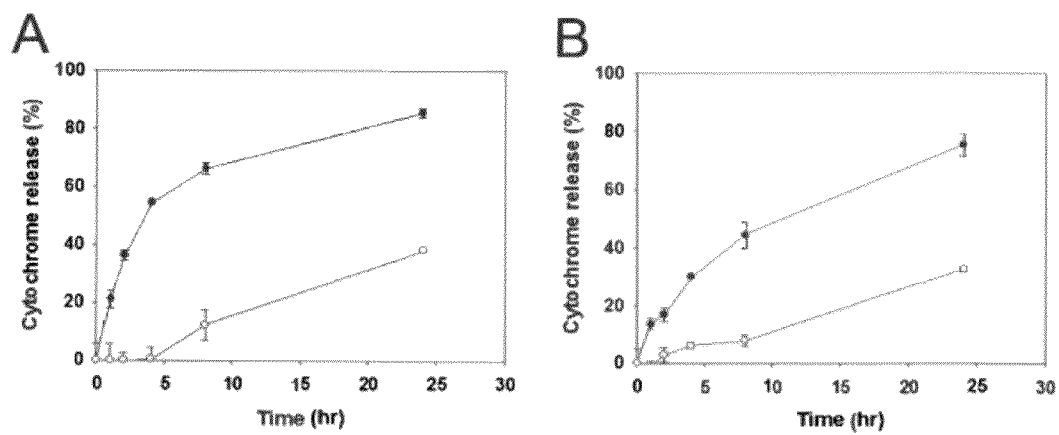
FIG. 4 shows the release rate of cytochrome c derivatives from PIC micelles, as measured by fluorometry. More specifically, panel A shows PIC micelles obtained with the use of citraconic anhydride as a charge regulator, while panel B shows PIC micelles obtained with the use of cis-aconitic anhydride as a charge regulator. In the figure, open plots (◯; open circles) represent the release rate in a pH 7.4 environment (under physiological conditions), while closed plots (●; closed circles) represent the release rate in a pH 5.5 environment.

9. Breakdown (Dissociation) of PIC Micelles (FIG. 4)

The breakdown rate of PIC micelles was measured by the probe-probe quenching-dequenching method. PIC micelles composed of each Alexa-Fluor-labeled cytochrome c derivative and PEG-pAsp(DET) were prepared as described in 4 above. Assuming that total fluorescence intensity (I) was the sum of the intensity of free cytochrome c ($I_f$) and the intensity of cytochrome c derivative in PIC micelles ($I_m$), the following calculation equation was obtained.

$$I = I_f + I_m = I_{f0} \times \frac{x}{100} + I_{m0} \times \frac{100-x}{100}$$

$I_{f0}$: Fluorescence intensity of cytochrome c not complexed with the polymer (in free from)
$I_{m0}$: Initial fluorescence intensity of cytochrome c derivative in PIC micelles
x: Ratio of free cytochrome c The above equation can be used to calculate the ratio (x) of released cytochrome c. After the PIC micelles were incubated in buffer (pH 5.5 or pH 7.4), the fluorescence of each sample was measured with a Nanodrop® ND-3300 fluorospectrometer. The results obtained are shown in FIG. 4.

Figure 5:
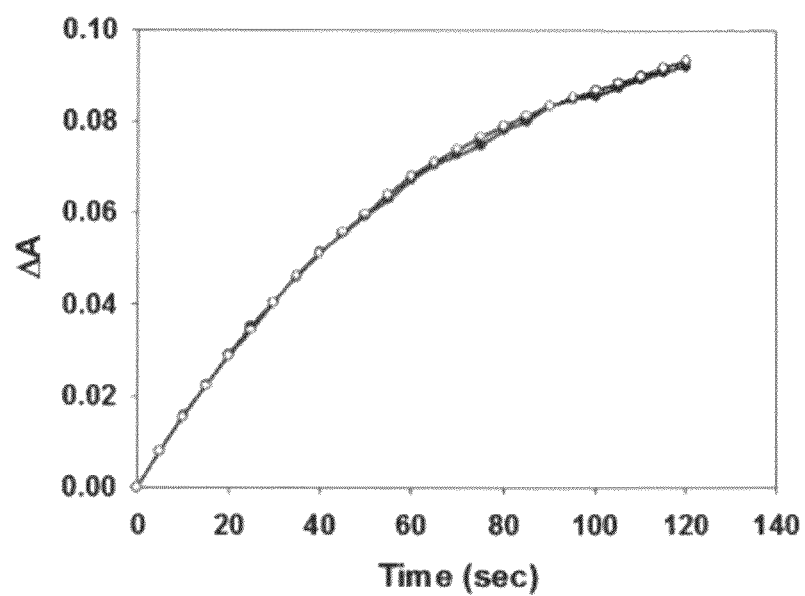
FIG. 5 shows the results measured for the oxidation activity of cytochrome c on ABTS (2,2'-azinobis(3-ethylbenzothiazoline-6-sulfonic acid)). In the figure, open plots (◯; open circles) represent the activity of cytochrome c released from PIC micelles obtained with the use of citraconic anhydride as a charge regulator, while closed plots (●; closed circles) represent the activity of wild-type cytochrome c.
Figure 6:
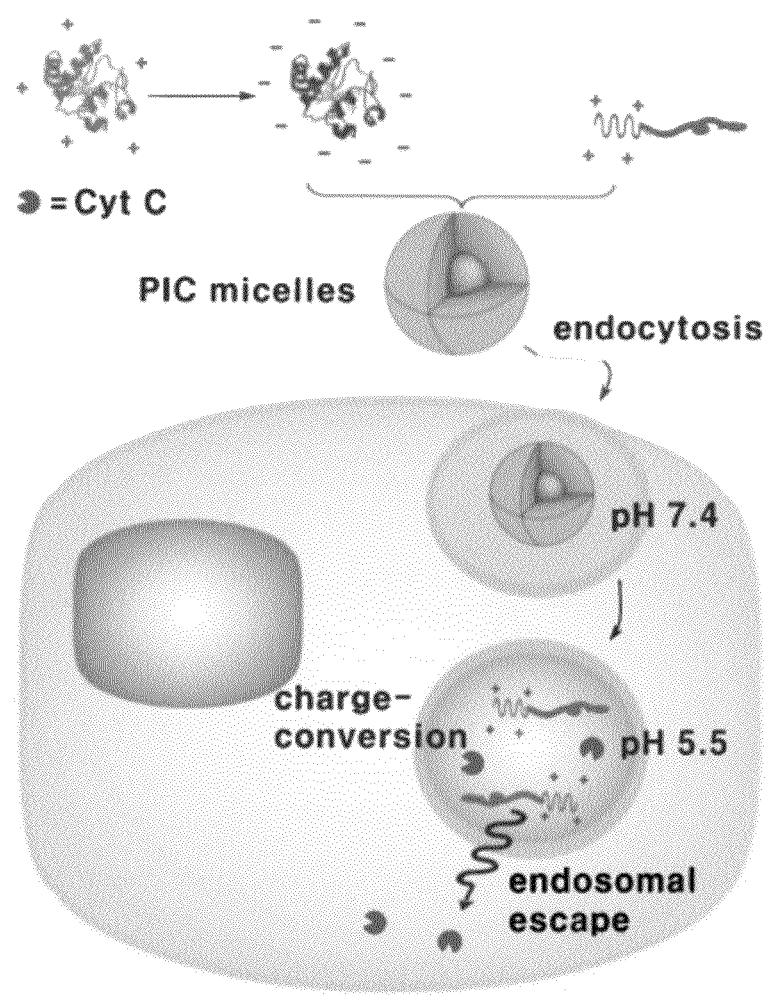
FIG. 6 schematically shows an intracellular protein delivery system mediated by charge-conversional PIC micelles.

10. Activity Comparison Between Wild-Type Cytochrome c and Cytochrome c Released from Pic Micelles (FIG. 5 and FIG. 6)

The electron transport activity of cytochrome c was measured by a catalytic conversion test on ABTS (2,2'-azinobis (3-ethylbenzothiazoline-6-sulfonic acid); WAKO. Japan) in Tris buffer. Equal amounts of cytochrome c and the cytochrome c derivative (CytC-Cit) (the amount of protein was determined by UV-visible absorption in the Soret band of cytochrome c) were each dissolved in distilled water, and PEG-pAsp(DET) was added as a cationic polymer for PIC micelle formation. To cause 100% release of the encapsulated protein, each sample was incubated in buffer at pH 5.5 for 48 hours and then added to Tris buffer (500 µL). The final pH and ionic strength were found to be 7.4 and 150 mM, respectively. Each mixture was transferred to a polystyrene cuvette, followed by addition of aqueous hydrogen peroxide ($H_2O_2$ conc.=25 mM) (500 µL), as in the case of Tris buffer. Subsequently, an ABTS solution in Tris buffer (ABTS conc.=1 mg/mL) was added in a volume of 500 µL. The absorbance (A) of the oxide at 418 nm was monitored every 5 seconds for 2 minutes to measure time-dependent changes in the absorbance. The results obtained are shown in FIG. 5.

Figure 7:
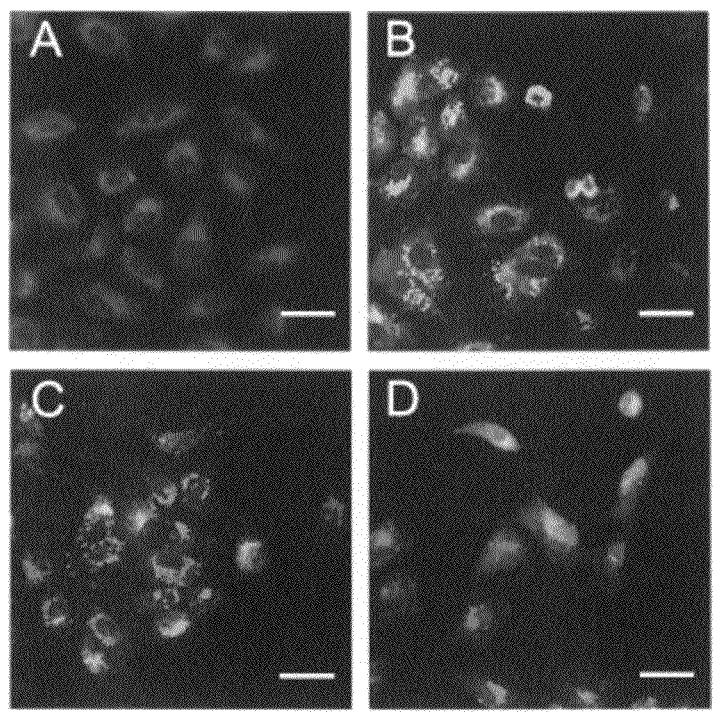
FIG. 7 shows images of HuH-7 cells receiving intracellular delivery of a given substance, as observed under a confocal laser scanning microscope (CLSM) (at 24 hours after transfection). More specifically, panel A shows intracellular delivery of wild-type cytochrome c in free form, panel B shows intracellular delivery of PIC micelles obtained with the use of succinic anhydride as a charge regulator (Cyt-Suc PIC micelles), panel C shows intracellular delivery of PIC micelles obtained with the use of cis-aconitic anhydride as a charge regulator (Cyt-Aco PIC micelles), and panel D shows intracellular delivery of PIC micelles obtained with the use of citraconic anhydride as a charge regulator (Cyt-Cit PIC micelles). Each cytochrome c derivative was labeled with Alexa Fluor 488 (green), and late endosomes and lysosomes were stained with LYSOTRACKER Red (red). The white scale bars in the figure each represent 50 µm.
Figure 8:
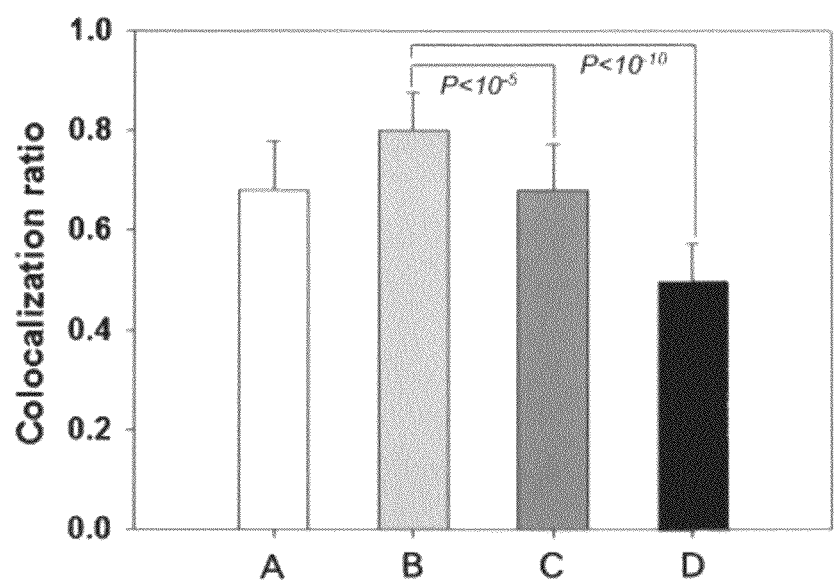
FIG. 8 shows the results analyzed for co-localization of Alexa Fluor 488 fluorescence (green) from fluorescnetly labeled cytochrome c derivatives and LYSOTRACKER Red fluorescence (red). More specifically, A shows the results of wild-type cytochrome c in free form, B shows the results of PIC micelles obtained with the use of succinic anhydride as a charge regulator (Cyt-Suc PIC micelles), C shows the results of PIC micelles obtained with the use of cis-aconitic anhydride as a charge regulator (Cyt-Aco PIC micelles), and D shows the results of PIC micelles obtained with the use of citraconic anhydride as a charge regulator (Cyt-Cit PIC micelles). Each error bar represents standard deviation measured on 20 cells.

11. In Vitro Protein Delivery into HuH-7 Cells (FIG. 7 and FIG. 8)

Human papilloma (HuH-7) cells were seeded in 8-chamber cover slips and incubated overnight in 200 µL of Dulbecco's modified Eagle's medium (DMEM) (10% FBS). Micelles encapsulating wild-type cytochrome c (CytC) or the cytochrome c derivative (Cyt-Suc, Cyt-Cit or Cyt-Aco) were prepared in the same manner as described in 4 above. Each sample (0.1 µM CytC) (20 µL) was introduced into wells and incubated at 37° C. After incubation for 24 hours, the medium was removed and the cells were washed twice with PBS. For determination of delivery into the cells, acidic late endosomes and lysosomes stained with LYSOTRACKER Red (MOLECULAR PROBES, USA) were observed under a confocal laser scanning microscope (CLSM). For observation under a CLSM, an Axiovert 100M (CARL ZEISS, Germany) equipped with a 40× magnification objective lens (Plan-Apochromat, CARL ZEISS, Germany) was used and the samples were irradiated at excitation wavelengths of 488 nm (argon laser) and 633 nm (helium-neon laser). It should be noted that the 488 nm wavelength was used for excitation of Alexa Fluor 488, while the 633 nm wavelength was used for excitation of LysoTraker Red. As a result, as shown in FIG. 7, wild-type cytochrome c (A) was less taken up by the cells. The PIC micelles obtained with the use of succinic anhydride which is not responsive to low pH environment (B) were taken up by the cells, but they were confirmed to give low efficiency of endosomal escape (green fluorescence is co-localized with red fluorescence from LYSOTRACKER). In contrast, in the case of the PIC micelles obtained with the use of cis-aconitic anhydride and citraconic anhydride responsive to low pH environment (C and D, respectively), green fluorescence was found in the cytoplasm, confirming that cytochrome c efficiently escaped from endosomes to the cytoplasm. Moreover, FIG. 8 shows the results of more quantitative analysis, in which the vertical axis represents the ratio of the number of pixels between red fluorescence and green fluorescence. As a result, C and D showed a reduction in this ratio, indicating that Alexa Fluor 488-labeled cytochrome c escaped from endosomes.

These results demonstrate that once the PIC taken up into the cells reaches endosomes, the charge regulator is eliminated to cause a change in the charge balance within the PIC, whereby the PIC is broken down, as a result of which the polymer damages the endosomal membrane, while cytochrome c released from the PIC migrates into the cytoplasm.

Figure 9:
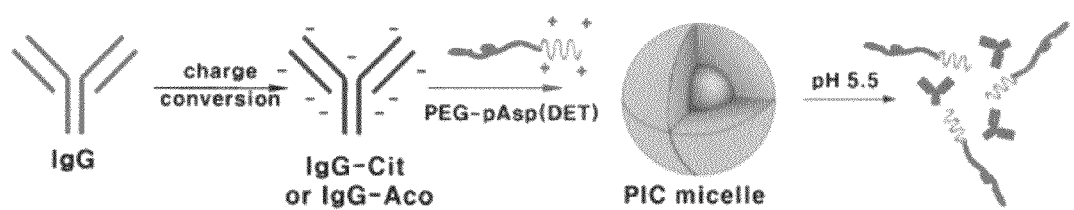
FIG. 9 schematically shows how to prepare a charge-conversional PIC micelle using charge-conversional IgG.

12. PIC Micelles Encapsulating Charge-Conversional Antibody Protein (FIG. 9)

The antibody protein used was immunoglobulin G (IgG; molecular weight: >150 kDa). For charge conversion of IgG, (i) $NaN_3$ in a stock solution of Alexa-Fluor 488-labeled IgG was first removed on a gel filtration column (ii) The IgG was dissolved in 0.1 M $NaHCO_3$ (pH 9.0) buffer. (iii) To this solution, citraconic anhydride or cis-aconitic anhydride was added. (iv) The resulting mixture was purified on a gel filtration column. An IgG derivative whose overall charge was regulated (IgG-Cit or IgG-Aco) was obtained.

This IgG derivative (IgG-Cit or IgG-Aco) was used as a protein to be encapsulated, and the same procedure as described in 4 above was repeated to prepare PIC micelles. The PIC micelles thus prepared were delivered into cells. The preparation of these PIC micelles is summarized in FIG. 9.

Figure 10:
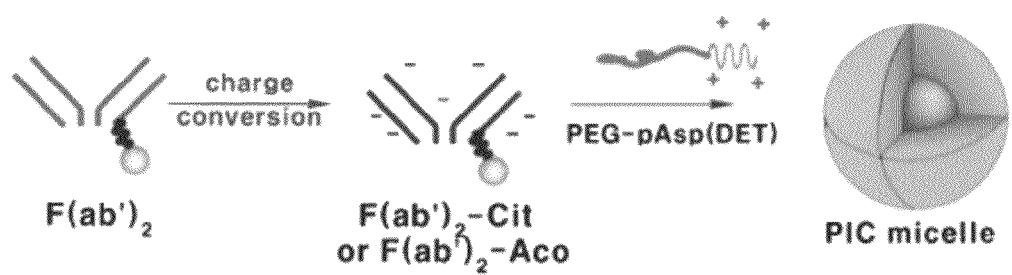
FIG. 10 schematically shows how to prepare a charge-conversional PIC micelle using charge-conversional F(ab')$_2$.
Figure 11:
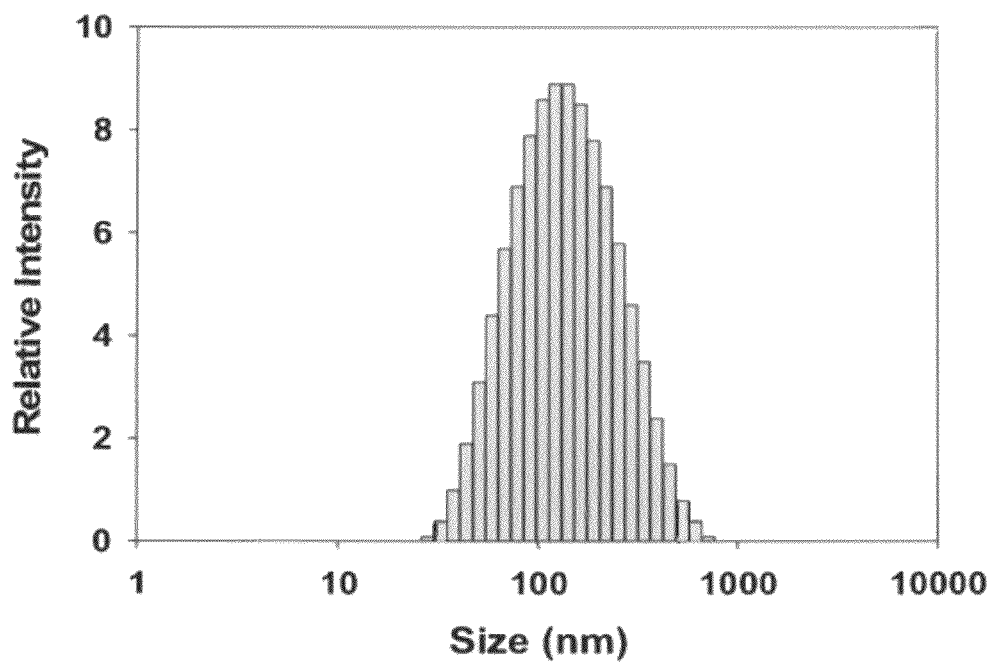
FIG. 11 shows the particle size distribution of F(ab')$_2$-encapsulating PIC micelles, as measured by dynamic light scattering (DLS).

13. PIC Micelles Encapsulating Charge-Conversional Antibody Fragment (F(ab')$_2$) (FIG. 10 and FIG. 11)

For charge conversion of an antibody fragment F(ab')$_2$, (i) $NaN_3$ in a stock solution of Alexa-Fluor 488-labeled F(ab')$_2$ was first removed on a gel filtration column. (ii) The F(ab')$_2$ was dissolved in 0.1 M $NaHCO_3$ (pH 9.0) buffer. (iii) To this solution, citraconic anhydride or cis-aconitic anhydride was added. (iv) The resulting mixture was purified on a gel filtration column. An F(ab')$_2$ derivative whose overall charge was regulated (F(ab')$_2$-Cit or F(ab')$_2$-Aco) was obtained.

This F(ab')$_2$ derivative (F(ab')$_2$-Cit or F(ab')$_2$-Aco) was used as a protein to be encapsulated, and the same procedure as described in 4 above was repeated to prepare PIC micelles. The preparation of these PIC micelles is summarized in FIG. 10. The PIC micelles were also measured for their particle size (particle size distribution) in the same manner as described in 6 above. The results obtained are shown in FIG. 11.

Figure 12:
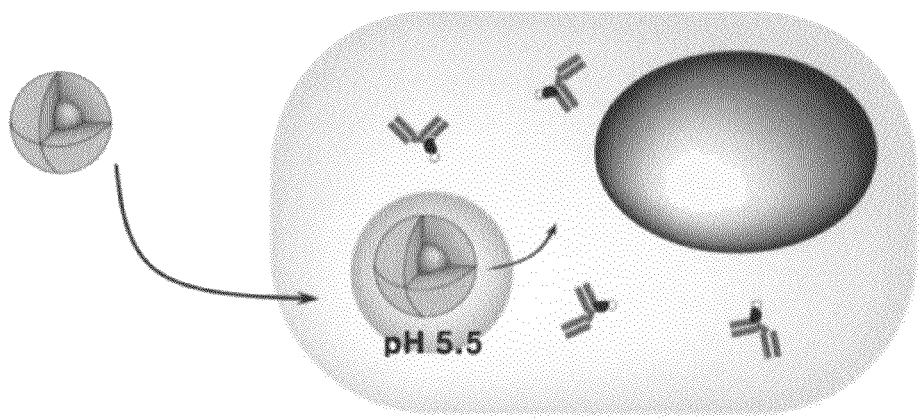
FIG. 12(A) schematically shows intracellular delivery of F(ab')$_2$ mediated by charge-conversional PIC micelles.
FIG. 12(B) shows images of HeLa cells receiving PIC micelle-mediated intracellular delivery, as observed under a confocal laser scanning microscope (CLSM).
Figure 12:
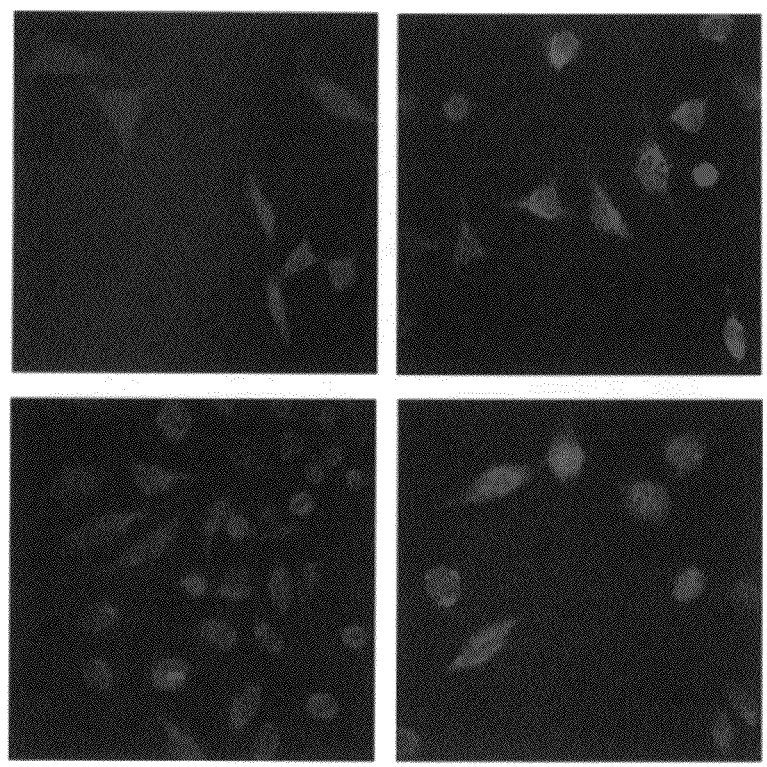

Moreover, as schematically shown in FIG. 12(A), these PIC micelles were provided for intracellular delivery of F(ab')$_2$. More specifically, the PIC micelles prepared above were used to deliver F(ab')$_2$ into HeLa cells, and the cells receiving delivery were observed under a confocal laser scanning microscope (CLSM). The results obtained are shown in FIG. 12(B).

Example 2

1. Materials

N,N-Dimethylformamide (DMF) (WAKO, Wako Pure Chemical Industries, Ltd., Japan)
Dichloromethane (DCM) (WAKO, Japan)
Tetrahydrofuran (THF) (WAKO, Japan)
n-Hexane (WAKO, Japan)

Triethylamine (TEA) (Tokyo Chemical Industry Co. Ltd., Japan)

Diethylenetriamine (DET; bis(2-aminoethyl)amine), which was purchased from Tokyo Chemical Industry Co. Ltd. (Japan) and distilled again before use.

Methanesulfonyl chloride (MsCl), acetic acid, citraconic anhydride, succinic anhydride and hydrochloric acid, which were purchased from WAKO, (Japan) and used without further purification.

6-Bromo-1-hexanol, sodium azide, sodium hydroxide, lithium aluminum hydride (LAH), 1-methyl-2-pyrrolidinone (NMP) and cis-aconitic anhydride, which were purchased from ALDRICH (USA).

α-Methoxy-ω-aminopoly(ethylene glycol) (molecular weight=12,000) and β-benzyl-L-aspartate-N-carboxy-anhydride (BLA-NCA), which were available from NOF Corporation (Japan).

Anti-nuclear pore complex (NPC) antibody (Clone 414), which was purchased from SIGMA (USA).

Alexa Fluor 488-labeled anti-mouse IgG (Fab')$_2$ fragment, which was purchased from Invitrogen (USA).

2. Synthesis of Cationic Polymer

As a cationic polymer having a PEG moiety and a polycation moiety, PEG-C6-pAsp(DET) (PEG-C6-{N—[N'-(2-aminoethyl)-2-aminoethyl]aspartamide}) was synthesized in the following manner (see Scheme 2 shown below).

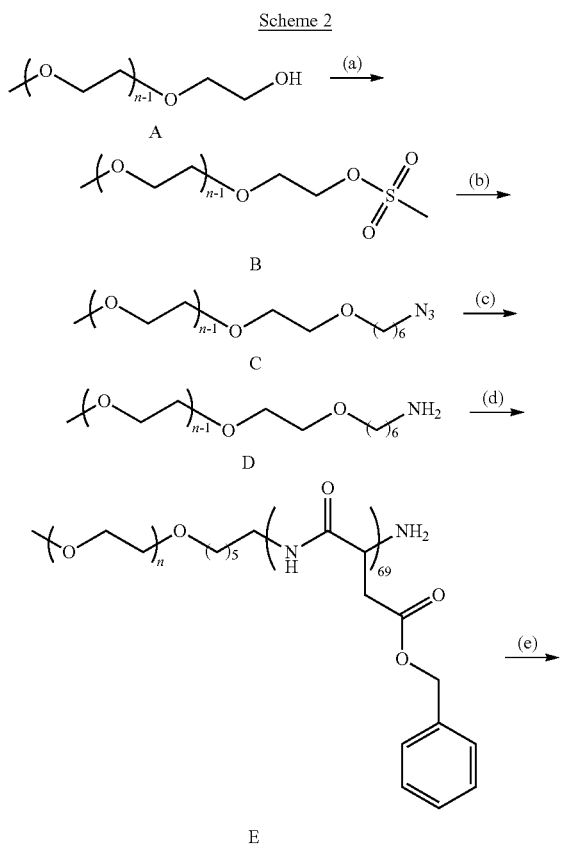

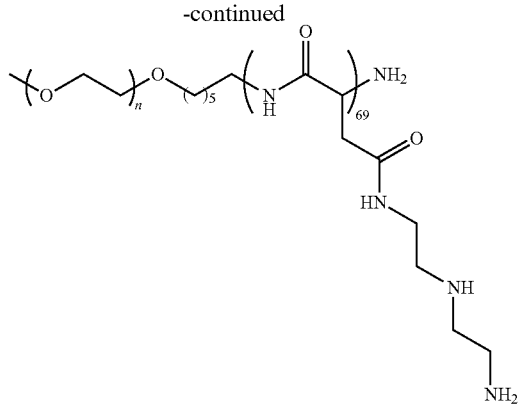

F (a) MsCl, DCM
(b) 6-Azido-1-hexanol/NaH, THF
(c) LAH, THF
(d) BLA-NCA, DMF/DCM
(e) DET, NMP

(1) Synthesis of PEG-Ms (PEG-mesylate) (B in Scheme 2)

α-Methoxy-ω-aminopoly(ethylene glycol) (molecular weight=12,000) (A in Scheme 2) (3.0 g; 0.25 mmol) was dissolved in dry THF (20 mL). After stirring at 40° C. for 30 minutes, 160 µL of TEA (1.13 mmol) was added to this solution. Then, 10 mL of THF containing MsCl (68 µL; 0.875 mmol) was added dropwise to the above solution. After stirring at 40° C. for 30 minutes, the mixed solution was further stirred at room temperature for 2.5 hours. The product (PEG-Ms) was precipitated in 450 mL hexane and then dried. The yield was 99% or more.

All NMR spectra were recorded at 300 MHz with a JEOL EX 300 spectrometer. Chemical shifts were reported in ppm down field from tetramethylsilane.

$^1$H NMR (CDCl$_3$): δ3.1 (3H, O$_3$SCH$_3$), δ3.4 (3H, CH$_3$OCH$_2$CH$_2$), δ3.6 (1092H, OCH$_2$CH$_2$O), δ4.4 (2H, OCH$_2$CH$_2$O$_3$SCH$_3$).

(2) Synthesis of 6-azido-1-hexanol

6-Bromo-1-hexanol (5.00 g, 27.6 mmol) was dissolved in 12 mL of DMF. To this solution, sodium azide (4.00 g, 61.5 mmol) was added and the mixture was stirred at 50° C. for 3 days. The mixture was concentrated by evaporation, and distilled water (10 mL) was added thereto. This aqueous solution was extracted six times with diethyl ether, and the combined organic extracts were dried over magnesium sulfate, followed by evaporation to give a product (6-azido-1-hexanol). The yield was 99% or more.

$^1$H NMR (CDCl$_3$): δ1.4-1.8 (9H, N$_3$CH$_2$(CH$_2$)$_4$CH$_2$OH), δ3.3 (2H, N$_3$CH$_2$(CH$_2$)$_4$CH$_2$OH), δ3.7 (2H, N$_3$CH$_2$(CH$_2$)$_4$CH$_2$OH).

(3) Synthesis of PEG-C6-azide (C in Scheme 2)

6-Azido-1-hexanol obtained in (2) above was dissolved in dry THF (4 mL) containing 68 mg of sodium hydride (1.7 mmol), and then stirred for 1 hour. PEG-Ms (1.3 g, 0.11 mmol) obtained in (1) above was dissolved in dry THF (10 mL), and to this solution, the solution of 6-azido-1-hexanol prepared above was added. After stirring at 50° C. for 3 days, distilled water (20 mL) was added to the mixture. The mixture was extracted with DCM and the organic layer was dried over magnesium sulfate. After the organic layer was concentrated to 20 mL, the product (PEG-C6-azide) was precipitated in hexane. The yield was 88% or more.

$^1$H NMR (CDCl$_3$): δ1.4 (4H, PEG-OCH$_2$CH$_2$(CH$_2$)$_2$CH$_2$CH$_2$N$_3$), δ1.7 (4H, PEG-OCH$_2$CH$_2$(CH$_2$)$_2$CH$_2$CH$_2$N$_3$), δ3.3 (2H, PEG-O(CH$_2$)$_5$CH$_2$N$_3$), δ3.4 (3H, CH$_3$OCH$_2$CH$_2$), δ3.5 (2H, PEG-OCH$_2$(CH$_2$)$_5$N$_3$), δ3.6 (1092H, OCH$_2$CH$_2$O).

(4) Synthesis of PEG-C6-amine (D in Scheme 2)

PEG-C6-azide (0.75 g, 0.063 mmol) obtained in (3) above was dissolved in dry THF (7 mL). To this solution, THF (2 mL) containing LAH (166 mg) was added dropwise, and the mixture was stirred at room temperature for 24 hours. Ethyl acetate (20 mL) was added to the stirred solution, and this mixture was diluted with a large volume of DCM. After filtration of precipitates, the filtrate was concentrated. The final product (PEG-C6-amine) was obtained by being precipitated in ether. The yield was about 88%.

$^1$H NMR (CDCl$_3$): δ1.4-1.8 (10H, PEG-OCH$_2$(CH$_2$)$_4$CH$_2$NH$_2$), δ2.9 (2H, PEG-O(CH$_2$)$_5$CH$_2$NH$_2$), δ3.4 (3H, CH$_3$OCH$_2$CH$_2$), δ3.5 (2H, PEG-OCH$_2$(CH$_2$)$_5$NH$_2$), δ3.6 (1092H, OCH$_2$CH$_2$O).

(5) Synthesis of PEG-C6-PBLA (PEG-C6-poly(β-benzyl-L-aspartate)) (E in Scheme 2)

PEG-C6-PBLA can be obtained by ring-opening polymerization of BLA-NCA, starting from the terminal amino group of PEG-C6-amine obtained in (4) above. This PEG-C6-amine (150 mg; 0.0125 mmol) serving as a PEG macro-initiator was dissolved in 2 mL of DCM. 3 mL of DMF/DCM (1:5) containing BLA-NCA (250 mg; 1.0 mmol) was added to the PEG macro-initiator solution, and the reaction mixture was stirred under an argon atmosphere at 35° C. for 48 hours. The resulting polymer was precipitated in diethyl ether (100 mL). The GPC chromatogram of the converted PEG-pAsp showed a single mode, and $M_w/M_n$ was determined to be 1.16 from a calibration curve of PEG standards. Based on $^1$H NMR data (see below), the polymerization degree (DP) of BLA units was calculated to be 69.

$^1$H NMR (d$^6$-DMSO): δ2.6-3.1 (138H, COCHCH$_2$COOCH$_2$Ph), δ3.6 (1092H, OCH$_2$CH$_2$O), δ4.7 (69H, COCHNH), δ5.0 (138H, COOCH$_2$Ph), δ7.2 (345H, COOCH$_2$Ph), δ8.2 (69H, COCHNH).

(6) Synthesis of PEG-C6-pAsp(DET) (F in Scheme 2)

PEG-C6-PBLA (100 mg; 0.27 mmol of benzyl ester) obtained in (5) above was dissolved in NMP (5 mL). To this solution, diethylenetriamine (13 mmol) was added and the mixture was stirred at 10° C. for 2 hours. The resulting solution was added dropwise to a 10% aqueous acetic acid solution (10 mL). The neutralized solution was dialyzed at 4° C. against 0.01 M hydrochloric acid (three times) and distilled water (three times). As a lyophilized hydrochloride salt, a white powder of PEG-C6-pAsp(DET) was obtained. In $^1$H NMR (see below), there was no peak for benzyl groups.

$^1$H NMR (D$_2$O): δ2.7 (276H, COCHCH$_2$CONHCH$_2$CH$_2$NHCH$_2$CH$_2$NH$_2$, COCH$_2$CHCONHCH$_2$CH$_2$NHCH$_2$CH$_2$NH$_2$ and COCHCH$_2$CONHCH$_2$CH$_2$NHCH$_2$CH$_2$NH$_2$), δ2.9 (138H, COCHCH$_2$CONHCH$_2$CH$_2$NHCH$_2$CH$_2$NH$_2$), δ3.0 (138H COCHCH$_2$CONHCH$_2$CH$_2$NHCH$_2$CH$_2$NH$_2$), δ3.3 (141H, CH$_3$OCH$_2$CH$_2$ and COCHCH$_2$CONHCH$_2$CH$_2$NHCH$_2$CH$_2$NH$_2$), δ3.6 (1092H, OCH$_2$CH$_2$O).

3. Modification (Overall Charge Conversion) of Antibody and Others

Anti-nuclear pore complex (anti-NPC) IgG antibody (or Alexa Fluor 488-labeled anti-mouse IgG (Fab')$_2$ fragment) (200 to 300 μg) was dissolved in 0.1 M NaHCO$_3$ buffer (pH 9.0, 1 mL) and stirred at 4° C. for 30 minutes, followed by addition of citraconic anhydride (1 mg). After stirring for 2 hours, the mixture was purified with an Amicon Ultra (MWCO=10,000; MILLIPORE (Billerica, Mass.)) (using three volumes of distilled water). As a product, an IgG derivative (IgG-Cit) was obtained, which was modified to have citraconic amide by binding citraconic anhydride to the above IgG (see FIG. 13). A concentrate of IgG-Cit was quantified with a Micro BCA™ Protein Assay Reagent Kit (Pierce).

Figure 13:
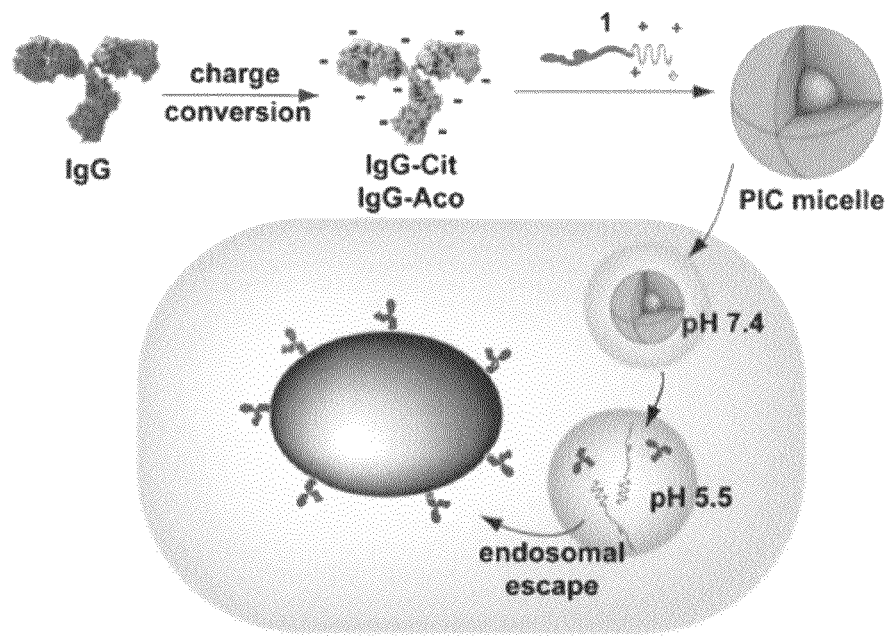
FIG. 13 schematically shows how to prepare a charge-conversional polyion complex micelle. More specifically, citraconic anhydride or cis-aconitic anhydride serving as a charge regulator is bound to an amine of a lysine residue in the IgG antibody protein to prepare IgG whose overall charge is converted to negative (hereinafter referred to as a IgG derivative), and this IgG derivative and a given block copolymer (PEG-C6-pAsp(DET)) serving as a cationic polymer are used to prepare polyion complex (PIC) micelles in a state encapsulating the derivative. This figure also shows that when the PIC micelles are then placed in a pH 5.5 environment, the micelles are broken down and citraconic anhydride or cis-aconitic anhydride bound as a charge regulator is eliminated from the encapsulated IgG derivative, as a result of which the derivative is regenerated into the original IgG (i.e., recovers its functions as IgG antibody).
Figure 13:
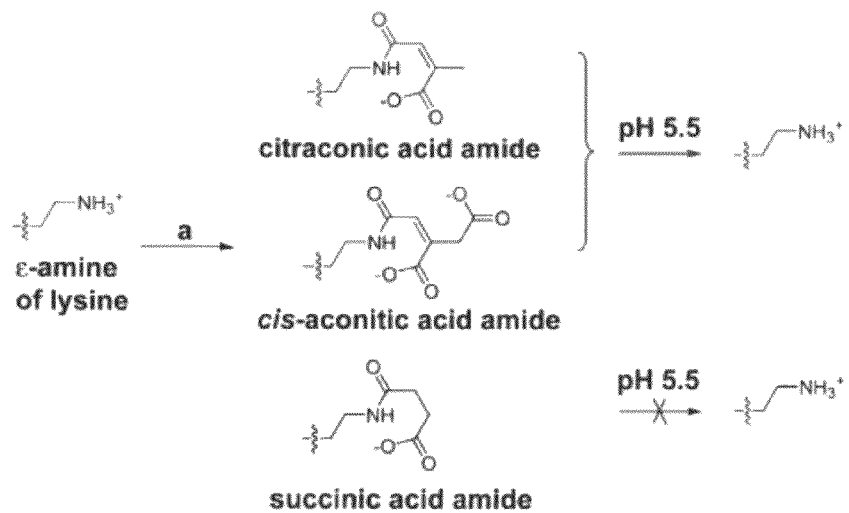
Figure 13:
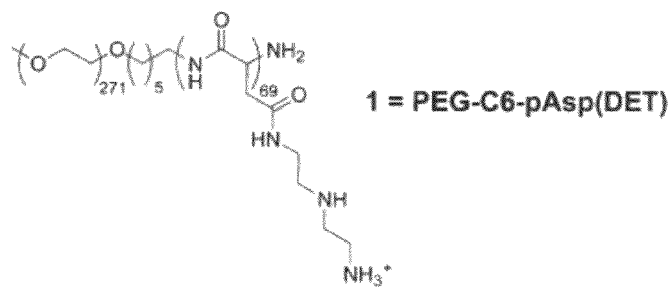

Except that citraconic anhydride was replaced with cis-aconitic anhydride and succinic anhydride, the same procedure was repeated to give an IgG derivative (IgG-Aco) which was modified to have cis-aconitic amide by binding cis-aconitic anhydride to the above IgG, as well as an IgG derivative (IgG-Suc) which was modified to have succinic amide by binding succinic anhydride to the above IgG (see FIG. 13).

It should be noted that IgG (Fab')$_2$ fragment derivatives (i.e., (Fab')$_2$-Cit, (Fab')$_2$-Aco and (Fab')$_2$-Suc) were also obtained in the same manner as in the case of the above IgG derivatives, except that the IgG antibody was replaced with the above anti-mouse IgG (Fab')$_2$ fragment.

4. Recovery of NPC Recognition

Figure 14A:
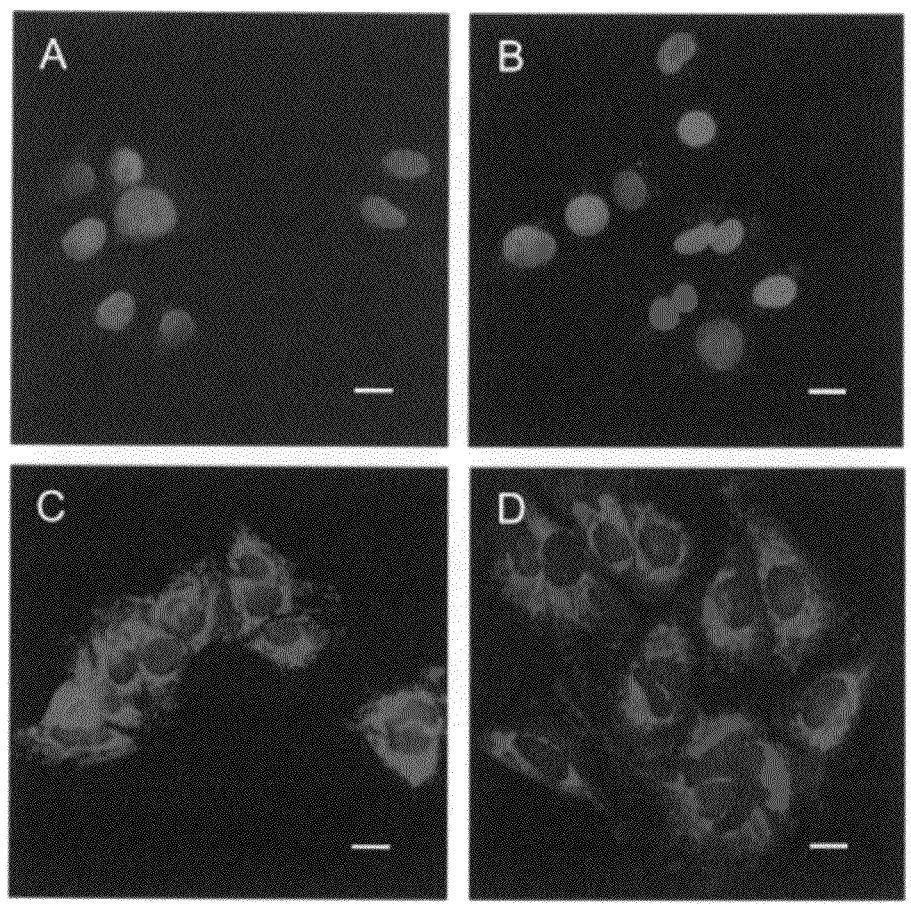
FIG. 14A shows recognition of nuclear pore complexes (NPCs) by anti-nuclear pore complex (anti-NPC) IgG derivatives. This figure shows images of Huh-7 cells treated with A) IgG-Aco (after 4 hour incubation at pH 7.4), B) IgG-Aco (after 3 hour incubation at pH 5.5), C) IgG-Suc (after 4 hour incubation at pH 7.4) or D) IgG-Suc (after 4 hour incubation at pH 5.5), as observed under a confocal laser scanning microscope (CLSM). Each IgG derivative is delivered into the paraformaldehyde-fixed cells after membrane permeation. Cell nuclei are stained with Hoechst 33258 (blue), while the IgG derivatives are detected with a secondary antibody, i.e., Alexa Fluor 488-labeled anti-mouse IgG (Fab')$_2$ fragment (green). The white scale bars in the figure each represent 20 µm.
Figure 14B:
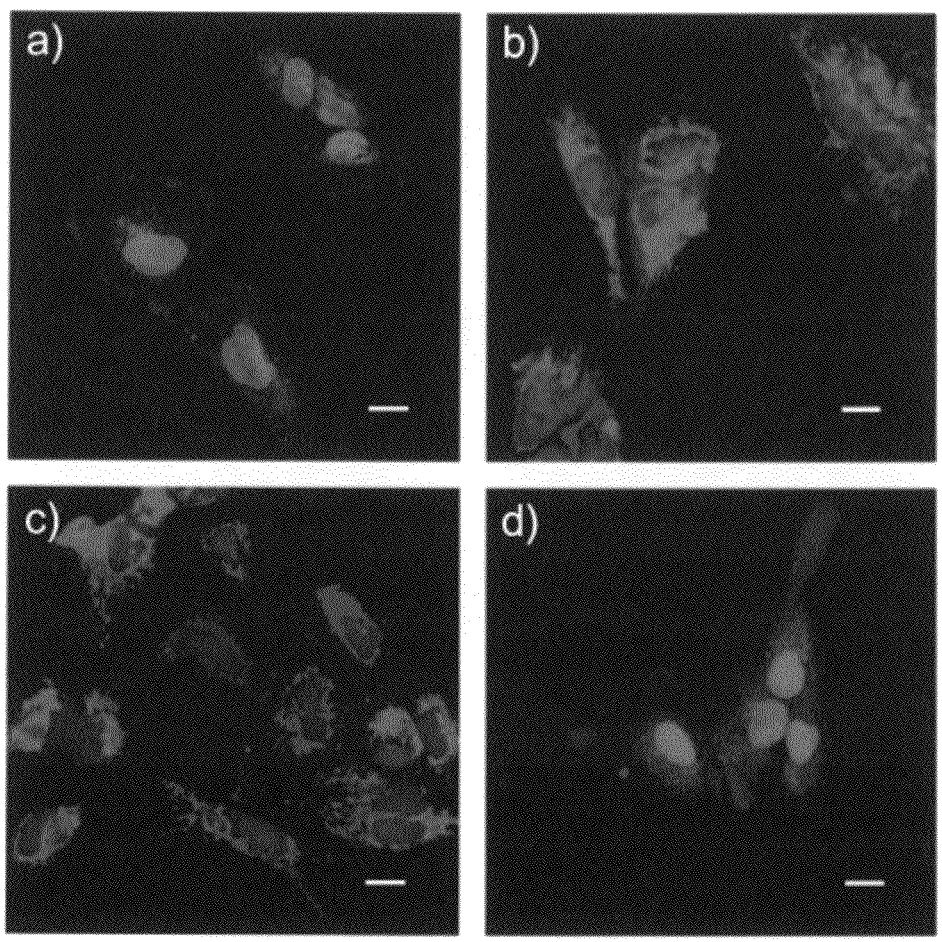
FIG. 14B shows recognition of nuclear pore complexes (NPCs) by anti-nuclear pore complex (anti-NPC) IgG derivatives. This figure shows images of Huh-7 cells treated with a) native IgG (unmodified IgG), b) IgG-Cit, c) IgG-Cit (after 4 hour incubation at pH 7.4) or d) IgG-Cit (after 4 hour incubation at pH 5.5), as observed under a confocal laser scanning microscope (CLSM). Each IgG derivative is delivered into the paraformaldehyde-fixed cells after membrane permeation. Cell nuclei are stained with Hoechst 33258 (blue), while the IgG derivatives are detected with a secondary antibody, i.e., Alexa Fluor 488-labeled anti-mouse IgG (Fab')$_2$ fragment (green). The white scale bars in the figure each represent 20 µm.

Human liver cancer (HuH-7) cells were seeded in 8-chamber cover slips and incubated overnight in 200 μL of Dulbecco's Modified Eagle Medium (DMEM) (10% FBS). These cells were fixed with 4% paraformaldehyde for 15 minutes, followed by membrane permeation with 0.2% Triton X-100 for 5 minutes. The fixed cells were treated with a 1% BSA solution for 10 minutes in order to avoid non-specific recognition, and then incubated in a 1% BSA solution at 37° C. for 1 hour together with each of the anti-NPC IgG derivatives (2 μg/mL; 15 nM) or other derivatives obtained in 3 above. These cells were treated with Alexa Fluor 488-labeled anti-mouse IgG (Fab')$_2$ fragment (4 μg/mL; 40 nM) serving as a secondary antibody in a 1% BSA solution at 37° C. for 1 hour. Cell nuclei were stained with Hoechst 33258. The cells were observed under a confocal laser scanning microscope (CLSM). For observation under a CLSM, an Axiovert 100M (CARL ZEISS, Germany) equipped with a 20× magnification objective lens (Plan-Apochromat, CARL ZEISS, Germany) was used and the samples were irradiated at wavelengths of 488 nm (argon laser) and 364 nm, which are excitation wavelengths for Alexa Fluor 488 and Hoechst 33258, respectively. The results obtained are shown in FIG. 14A and FIG. 14B.

5. Preparation of PICs

The cationic polymer (PEG-C6-pAsp(DET)) obtained in 2 above and the IgG derivative (IgG-Cit, IgG-Aco or IgG-Suc) or anti-mouse IgG (Fab')$_2$ fragment derivative ((Fab')$_2$-Cit, (Fab')$_2$-Aco or (Fab')$_2$-Suc) obtained in 3 above were used to prepare PIC micelles in the following manner.

The IgG derivative or anti-mouse IgG (Fab')$_2$ fragment derivative (0.10 mg/mL; 0.67 to 1.0 μM) and PEG-C6-pAsp (DET) (0.5 mg/mL) were each dissolved in distilled water.

The resulting respective solutions were each filtered through a 0.2 μm syringe filter and mixed together at a specific N/C ratio (more specifically N/C=2) to thereby obtain PIC micelles encapsulating the above IgG derivative or anti-mouse IgG (Fab')$_2$ fragment derivative. The term "N/C ratio" is used here to mean a ratio between the total number (N) of cationic groups (e.g., amino groups) in the block copolymer (PEG-C6-pAsp(DET) in this experiment) and the total number (C) of carboxyl groups in the charge-conversional protein (IgG derivative or anti-mouse IgG (Fab')$_2$ fragment derivative in this experiment).

It should be noted that in the following experiments, the above mixed solution was supplemented as appropriate with acetate buffer (pH 5.5) or phosphate buffer (pH 7.4). The final NaCl concentration in the mixed solution was set to 150 mM.

Figure 15:
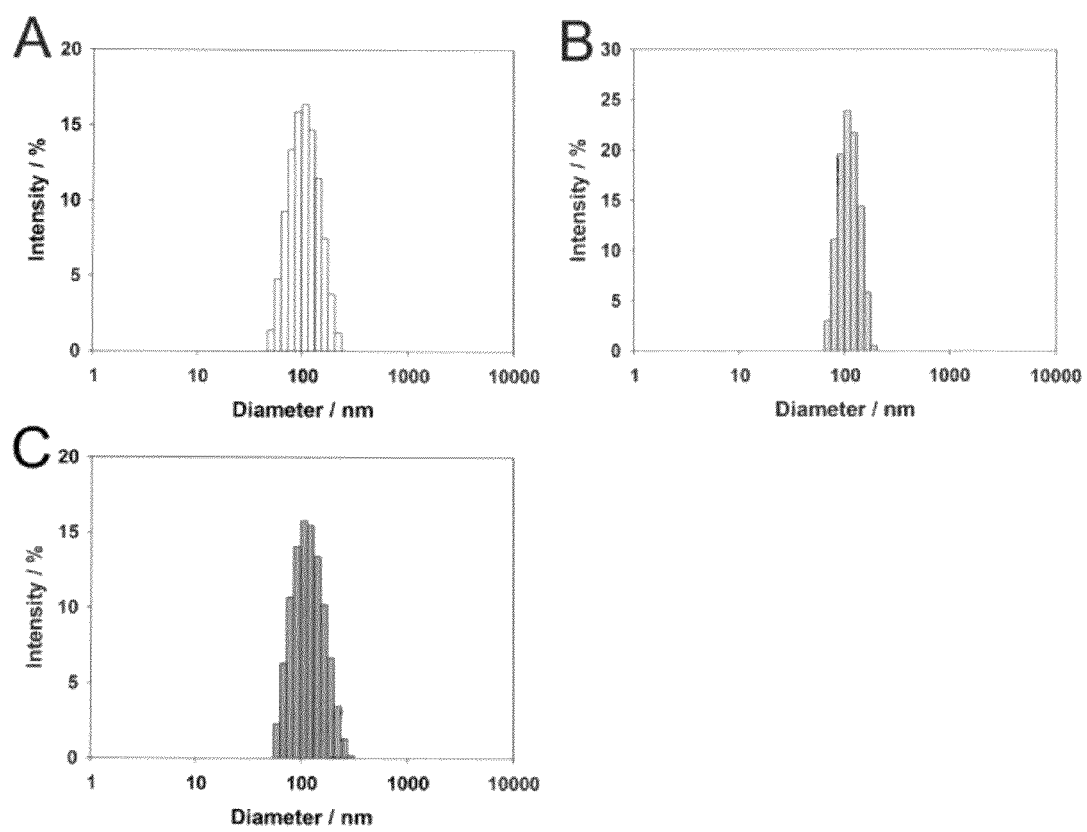
FIG. 15 shows the particle size distribution of PIC micelles encapsulating (A) IgG-Cit, (B) IgG-Aco or (C) IgG-Suc, as measured by dynamic light scattering (DLS). As a cationic polymer, PEG-C6-pAsp(DET) is used.
Figure 16:
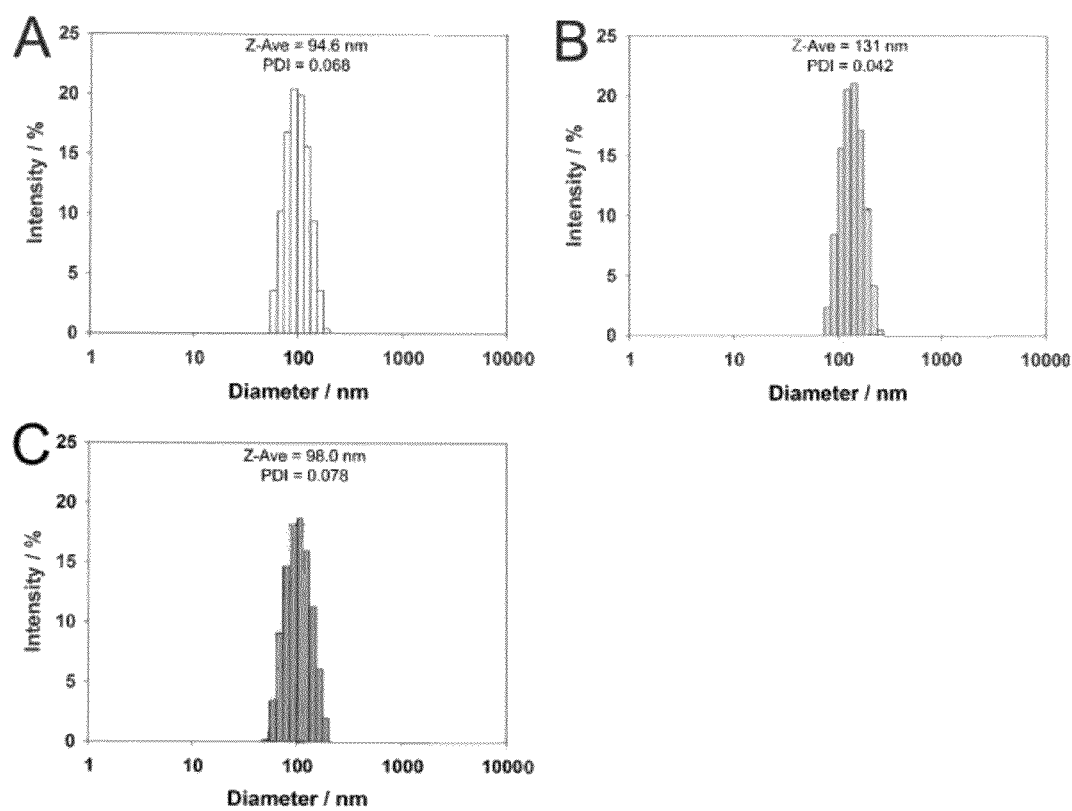
FIG. 16 shows the particle size distribution of PIC micelles encapsulating (A) (Fab')$_2$-Cit, (B) (Fab')$_2$-Aco or (C) (Fab')$_2$-Suc, as measured by dynamic light scattering (DLS). As a cationic polymer, PEG-C6-pAsp(DET) is used.

6. Particle Size Measurement of PIC Micelles by Dynamic Light Scattering (DLS) (FIGS. 15 and 16)

To measure the PIC micelles obtained in 5 above for their particle size (particle size distribution) by dynamic light scattering (DLS), each IgG derivative solution was adjusted to a final concentration of 25 μg/mL (0.17 to 0.25 μM). The measurement was conducted at 37° C. with a Zetasizer Nano-ZS (green badge, ZEN3500, MALVERN INSTRUMENTS, Malvern, Ltd. Malvern, U. K.) equipped with a 32 nm green laser. The results obtained are shown in FIGS. 15 and 16.

Moreover, the table below also shows the results obtained for the particle size and polydispersity index (PDI) of the PIC micelles, as measured by dynamic light scattering (DLS).

TABLE 2

| IgG derivative | Particle size (nm) | PDI |
|---|---|---|
| Anti-NPC IgG | N.D. | N.D. |
| Anti-NPC IgG-Cit | 98.3 | 0.096 |
| Anti-NPC IgG-Aco | 107 | 0.016 |
| Anti-NPC IgG-Suc | 111 | 0.121 |

Figure 17:
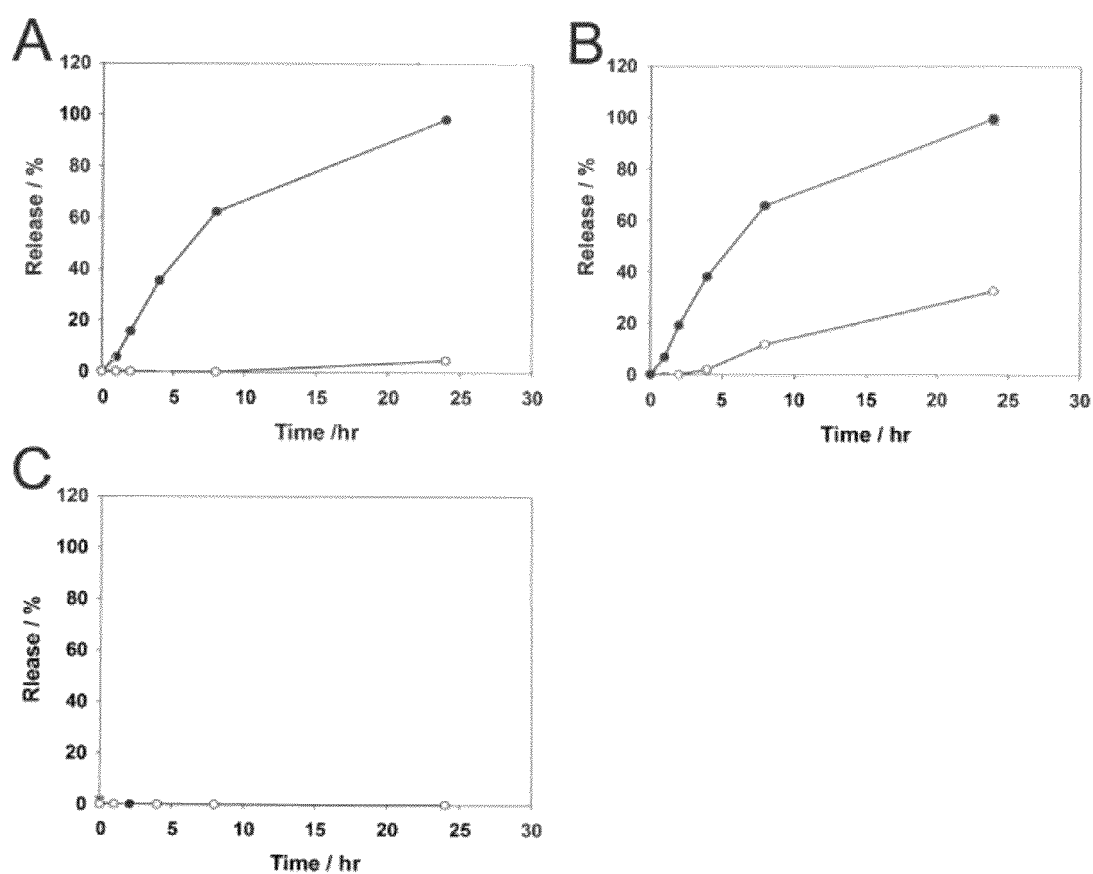
FIG. 17 shows the release rate of (Fab')$_2$ derivatives from PIC micelles, as measured by fluorometry. More specifically, panel A shows PIC micelles obtained with the use of citraconic anhydride as a charge regulator, panel B shows PIC micelles obtained with the use of cis-aconitic anhydride as a charge regulator, and panel C shows PIC micelles obtained with the use of succinic anhydride. In the figure, open plots (o; open circles) represent the release rate in a pH 7.4 environment (under physiological conditions), while closed plots (●; closed circles) represent the release rate in a pH 5.5 environment.

7. Breakdown (Dissociation) of PIC Micelles (FIG. 17)

The breakdown rate of PIC micelles was measured by the probe-probe quenching-dequenching method. PIC micelles composed of each Alexa-Fluor-labeled anti-mouse IgG (Fab')$_2$ fragment derivative and PEG-C6-pAsp(DET) were prepared as described in 5 above. Assuming that total fluorescence intensity (I) was the sum of the intensity of free anti-mouse IgG (Fab')$_2$ fragment ($I_f$) and the intensity of anti-mouse IgG (Fab')$_2$ fragment derivative in PIC micelle ($I_m$), the following calculation equation was obtained.

$$I = I_f + I_m = I_{f0} \times \frac{x}{100} + I_{m0} \times \frac{100-x}{100}$$

$I_{f0}$: Fluorescence intensity of anti-mouse IgG (Fab'), fragment not complexed with the polymer (in free from)

$I_{m0}$: Initial fluorescence intensity of anti-mouse IgG (Fab')$_2$ fragment derivative in PIC micelles x: Ratio of free anti-mouse IgG (Fab')$_2$ fragment The above equation can be used to calculate the ratio (x) of released antibody fragment (IgG (Fab')$_2$ fragment). After the PIC micelles were incubated in buffer (pH 5.5 or pH 7.4), the fluorescence of each sample was measured with a Nanodrop®ND-3300 fluorospectrometer. The results obtained are shown in FIG. 17.

8. Endosomal Escape of Antibody

Figure 18:
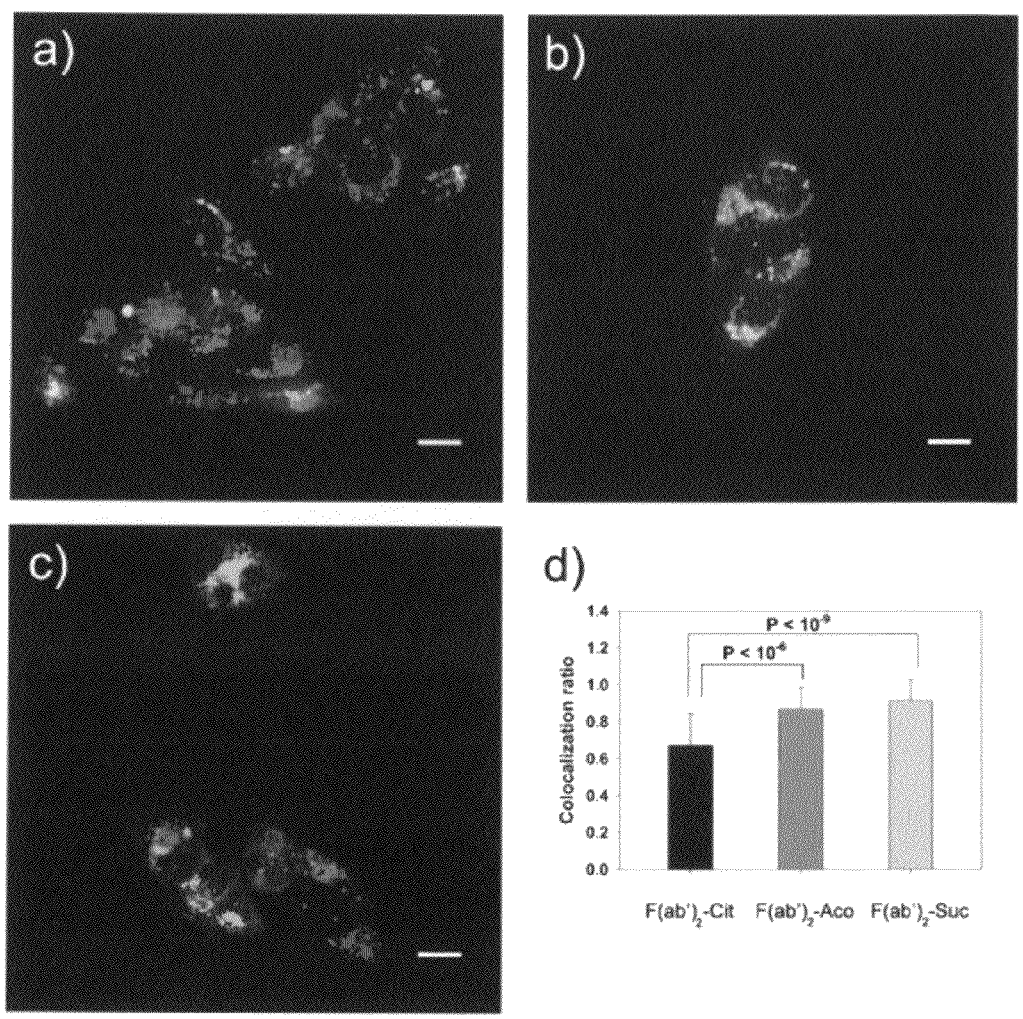
FIG. 18 shows images of HuH-7 cells receiving delivery of PIC micelles encapsulating Alexa Fluor 488-labeled anti-mouse IgG (Fab')$_2$ fragment derivatives (green), as observed under a confocal laser scanning microscope (CLSM). The derivatives used were a) (Fab')$_2$-Cit, b) (Fab')$_2$-Aco, and c) (Fab')$_2$-Suc. Late endosomes and lysosomes were stained with LYSOTRACKER Red (red). The white scale bars in the figure each represent 20 µm. Panel d) is a graph showing co-localization of green fluorescence from the (Fab')$_2$ derivatives and red fluorescence from LYSOTRACKER Red (error bar: standard deviation).

Human liver cancer (HuH-7) cells were seeded in 8-chamber cover slips and incubated overnight in 200 μL of Dulbecco's Modified Eagle Medium (DMEM) (10% FBS). PIC micelles encapsulating Alexa-Fluor-labeled (Fab')$_2$-Cit, (Fab')$_2$-Aco or (Fab')$_2$-Suc were prepared as described in 5 above. Each sample was added to wells and incubated at 37° C. The final concentration of each (Fab')$_2$ derivative was set to 5 μg/mL (50 nM). After incubation for 24 hours, the medium was removed and the cells were washed three times with PBS. After acidic late endosomes and lysosomes were stained with LYSOTRACKER Red (MOLECULAR PROBES, USA), their localization within the cells was observed under a confocal laser scanning microscope (CLSM). For observation under a CLSM, an Axiovert 100M (CARL ZEISS, Germany) equipped with a 20× magnification objective lens (Plan-Apochromat, CARL ZEISS, Germany) was used and the samples were irradiated at wavelengths of 488 nm (argon laser) and 633 nm, which are excitation wavelengths for Alexa Fluor 488 and LysoTraker Red, respectively. The results obtained are shown in FIG. 18.

9. NPC recognition by antibody in HuH-7 cells

Figure 19:
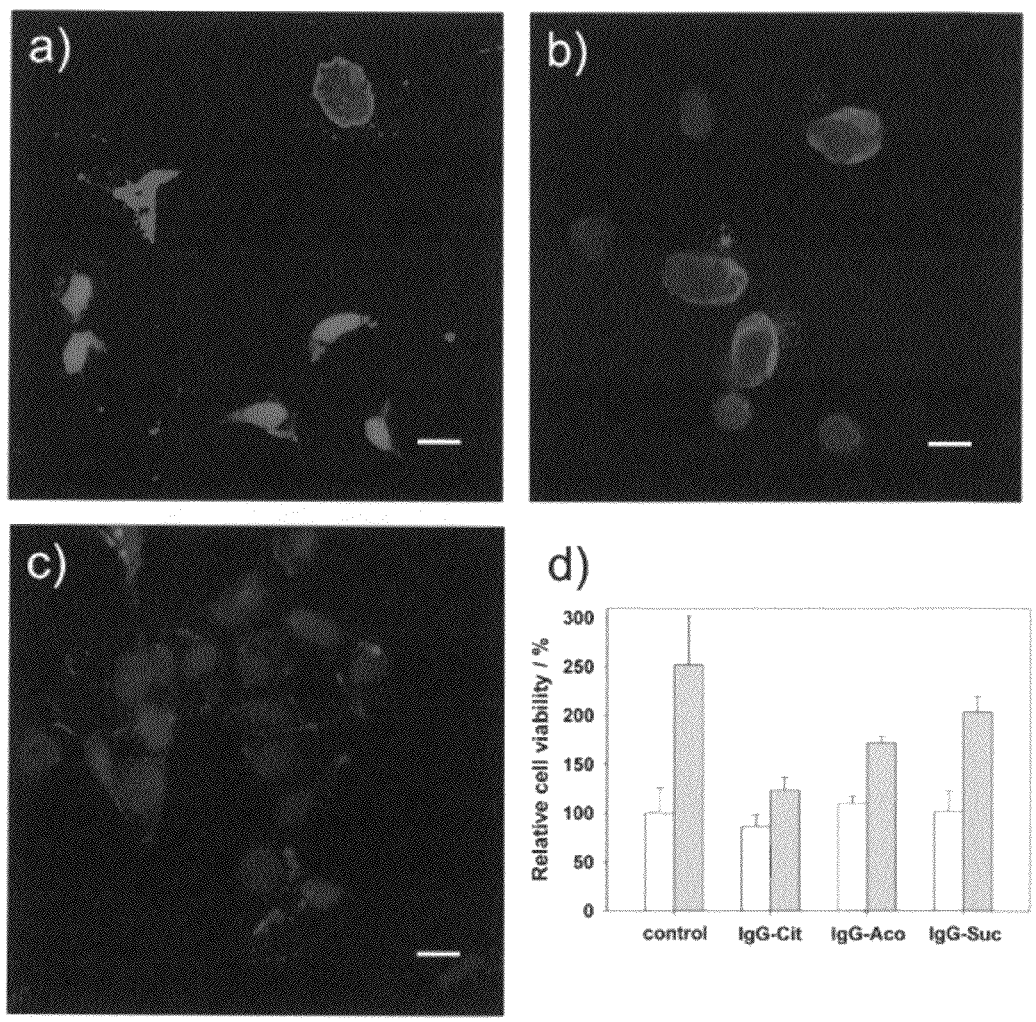
FIG. 19 shows images of HuH-7 cells receiving delivery of PIC micelles encapsulating IgG derivatives, as observed under a confocal laser scanning microscope (CLSM). The derivatives used were a) IgG-Cit, b) IgG-Aco, and c) IgG-Suc. Cell nuclei were stained with Hoechst 33258 (blue). The IgG derivatives were detected with a secondary antibody, i.e., Alexa Fluor 488-labeled anti-mouse IgG (Fab')$_2$ fragment (green). The white scale bars in the figure each represent 20 µm. Panel d) is a graph showing the cell growth ability of HuH-7 cells treated with each PIC micelle (receiving delivery of each PIC micelle), in which the white and gray bars represent cell viability after 24 hour incubation and cell viability after 48 hour incubation, respectively (error bar: standard deviation).

Human liver cancer (HuH-7) cells were seeded in 8-chamber cover slips and incubated overnight in 200 μL of Dulbecco's Modified Eagle Medium (DMEM) (10% FBS). PIC micelles encapsulating each IgG derivative (final concentration of IgG: 5 μg/mL (33 nM)) prepared as described in 5 above were added to the above HuH-7 cells. After incubation at 37° C. for 24 hours, these cells were fixed with 4% paraformaldehyde for 15 minutes, followed by membrane permeation with 0.2% Triton X-100 for 5 minutes. To avoid non-specific recognition, the fixed cells were treated with a 1% BSA solution for 10 minutes. For detection of the IgG derivatives, these cells were treated with Alexa Fluor 488-labeled anti-mouse IgG (Fab')$_2$ fragment (4 μg/mL; 40 nM) serving as a secondary antibody in a 1% BSA solution at 37° C. for 1 hour. Cell nuclei were stained with Hoechst 33258. The cells were observed under a confocal laser scanning microscope (CLSM). For observation under a CLSM, an Axiovert 100M (CARL ZEISS, Germany) equipped with a 20× magnification objective lens (Plan-Apochromat, CARL ZEISS, Germany) was used and the samples were irradiated at wavelengths of 488 nm (argon laser) and 364 nm, which are excitation wavelengths for Alexa Fluor 488 and Hoechst 33258, respectively. The results obtained are shown in FIG. 19 (particularly panels a to c).

10. Cell Growth Control by Antibody Delivery

To measure the cell growth ability of HuH-7 cells, these cells were incubated with each PIC micelle solution (final concentration of IgG: 10 μg/mL (67 nM)). After incubation for 24 and 48 hours, the cell viability of these cells was evaluated by MTT assay (Cell Counting Kit-9, Dojindo, Kumamoto, Japan). More specifically, the absorbance at 450 nm was measured for each well (according to the manufacturer's protocols) to thereby evaluate cell viability. The results obtained are shown in FIG. 19 (particularly panel d). The evaluation results were expressed as relative values (%) compared to the control cells (control) incubated in PBS (pH 7.4) simultaneously.

11. Discussion

The inventors of the present invention succeeded in delivering biologically active IgG antibodies into the cytoplasm for control of cell growth. In view of the fact that IgG antibodies have high selectivity to their target antigens, techniques of charge-conversional intracellular antibodies have high potential for bioimaging in living cells and for biological treatment against intracellular antigens. Furthermore, charge-conversional PIC micelles can be preferably applied to intravenous delivery of proteins, based on long-term stability in blood and high biocompatibility provided by PEG in the shell region of the PIC micelles.

INDUSTRIAL APPLICABILITY

The present invention enables the provision of a protein delivery means (e.g., a protein-encapsulating polymer micelle complex) which allows efficient introduction into cells (particularly into the cytoplasm), is highly stable in serum, and is also widely applicable. Moreover, the present invention enables the provision of a charge regulator for proteins, which is used for such a means. The present invention is particularly advantageous in facilitating intracellular delivery of proteins whose isoelectric point is in the alkaline to neutral range.

The protein delivery means of the present invention is extremely useful, for example, in that it can also be applied to various pharmaceutical compositions, such as protein formulations (e.g., antibody drugs and drugs for enzyme replacement therapy) and vaccine formulations.

The invention claimed is:

1. A polyion complex comprising a cationic polymer at least partially having a polycation moiety; and a protein whose overall charge is converted by a protein charge regulator;
    wherein the protein charge regulator comprises a compound represented by the following formula (I):

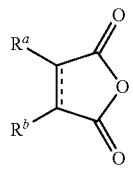
(I)

wherein $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group; alternatively, $R^a$ and $R^b$ may be linked to each other to form an aromatic ring or a cycloalkyl ring together with their adjacent carbon atoms; and a bond between the carbon atoms adjacent to $R^a$ and $R^b$, respectively, may be either a single bond or a double bond, and wherein the protein is not associated with an endosome membrane.

2. The polyion complex according to claim 1, wherein the polycation moiety is a polypeptide having cationic groups in its side chains.

3. The polyion complex according to claim 1, wherein the cationic polymer is represented by the following formula (1):

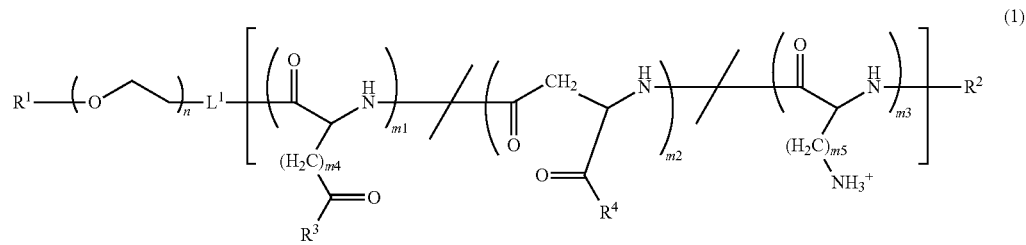
(1)

wherein $R^1$ and $R^2$ each independently represent a hydrogen atom or an optionally substituted linear or branched alkyl group containing 1 to 12 carbon atoms, $R^3$ and $R^4$ each represent a residue derived from an amine compound having a primary amine, $L^1$ represents NH, CO, or a group represented by the following formula (4):

$$-(CH_2)_{p1}-NH- \qquad (4)$$

wherein p1 represents an integer of 1 to 6, or a group represented by the following formula (5):

$$-L^{2a}-(CH_2)_{q1}-L^{3a}- \qquad (5)$$

wherein $L^{2a}$ represents OCO, OCONH, NHCO, NHCOO, NHCONH, CONH or COO, $L^{3a}$ represents NH or CO, and q1 represents an integer of 1 to 6, m1, m2 and m3 each independently represent an integer of 0 to 500 provided that the sum of m1, m2 and m3 represents an integer of 10 to 500, m4 represents an integer of 1 to 5, m5 represents an integer of 1 to 5, and n represents an integer of 0 to 500, and the symbol "/" means that m1+m2+m3 units of the respective monomers shown in the left and right sides of this symbol are sequenced in any order.

4. The polyion complex according to claim 3, wherein the group —$R^3$ and/or the group —$R^4$ in the polymer represents a group represented by the following formula (2):

$$-NH-(CH_2)_r-X^1 \qquad (2)$$

wherein $X^1$ represents an amine compound residue derived from a primary, secondary or tertiary amine compound or a quaternary ammonium salt, and r represents an integer of 0 to 5, or a group represented by the following formula (3):

$$-[NH-(CH_2)_s]_t-X^2 \qquad (3)$$

wherein $X^2$ represents an amine compound residue derived from a primary, secondary or tertiary amine compound or a quaternary ammonium salt, and s and t, which are independent of each other, represent an integer of 1 to 5 independently in each [NH—$(CH_2)_s$] unit and an integer of 2 to 5, respectively.

5. The polyion complex according to claim 4, wherein $R^3$ and/or $R^4$ is —NH—NH$_2$ or —NH—(CH$_2$)$_2$—NH—(CH$_2$)$_2$—NH$_2$.

6. The polyion complex according to claim 1, wherein the polycation moiety in the cationic polymer is bound to the protein through an electrostatic interaction.

7. The polyion complex according to claim 1, wherein the cationic polymer is a polymer further having a polyethylene glycol moiety,
wherein the protein and the polycation moiety in the cationic polymer form a core region, while the polyethylene glycol moiety in the cationic polymer forms a shell region around the core region.

8. The polyion complex according to claim 1, wherein the compound represented by formula (1) is dissociated from the protein released from the polyion complex upon introduction into cells, whereby the overall charge of the protein returns to its inherent charge.

9. A device for intracellular protein delivery comprising the polyion complex according to claim 1.

10. A kit for intracellular protein delivery comprising a cationic polymer at least partially having a polycation moiety and a protein charge regulator,
wherein the protein charge regulator comprises a compound represented by the following formula (I):

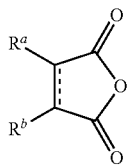
(I)

wherein $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group; alternatively, $R^a$ and $R^b$ may be linked to each other to form an aromatic ring or a cycloalkyl ring together with their adjacent carbon atoms; and a bond between the carbon atoms adjacent to $R^a$ and $R^b$, respectively, may be either a single bond or a double bond, and
wherein the protein is not associated with an endosome membrane.

11. The polyion complex according to claim 1, wherein the compound represented by formula (I) is at least one of the compounds represented by the following formulae (Ia) to (Ig).

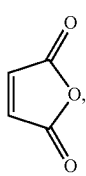
(Ia)

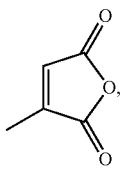
(Ib)

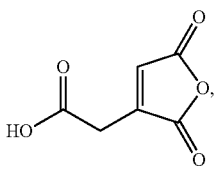
(Ic)

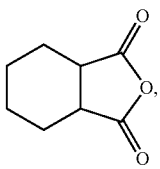
(Id)

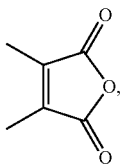
(Ie)

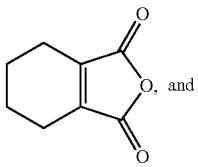
(If)

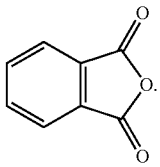
(Ig)

12. The polyion complex according to claim 1, wherein the protein charge regulator converts the overall charge of a basic or neutral protein into that of an acidic protein.

13. The polyion complex according to claim 1, wherein the protein charge regulator establishes binding between the compound represented by formula (I) and an amino group contained in the protein.

14. The polyion complex according to claim 1, wherein a mixing ratio (N/C ratio) between a total number (N) of cationic groups in the cationic polymer and a total number (C) of carboxyl groups in the protein is 0.1 to 200.

15. The polyion complex according to claim 1, wherein a particle size of the polyion complex is 5 to 200 nm.

16. The polyion complex according to claim 1, wherein the protein is an enzyme.

17. The polyion complex according to claim 1, wherein the protein is an antibody.

18. The polyion complex according to claim 1, wherein the protein is an antibody fragment selected from the group consisting of Fab, Fab', F(ab')$_2$, H chain, L chain, H chain V region, and L chain V region, scFv, scFv dimer, dsFv and fragments at least partially containing complementarity determining regions (CDRs).

\* \* \* \* \*